United States Patent
Fjaellskog et al.

(10) Patent No.: US 11,001,628 B2
(45) Date of Patent: May 11, 2021

(54) COMBINED USE OF ANTI PD-1 AND ANTI M-CSF ANTIBODIES IN THE TREATMENT OF CANCER

(71) Applicant: Novartis AG, Basel (CH)

(72) Inventors: Marie-Louise Fjaellskog, Lexington, MA (US); John Scott Cameron, Belmont, MA (US); Zhu Cao, Lawrenceville, NJ (US); Daniela Cipolletta, Arlington, MA (US); Kenzie MacIsaac, Brookline, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/879,064

(22) PCT Filed: Jul. 27, 2016

(86) PCT No.: PCT/IB2016/054487
§ 371 (c)(1),
(2) Date: Jan. 24, 2018

(87) PCT Pub. No.: WO2017/017623
PCT Pub. Date: Feb. 2, 2017

(65) Prior Publication Data
US 2018/0222973 A1 Aug. 9, 2018

Related U.S. Application Data

(60) Provisional application No. 62/352,637, filed on Jun. 21, 2016, provisional application No. 62/198,384, filed on Jul. 29, 2015.

(51) Int. Cl.
| | |
|---|---|
| *A61K 39/395* | (2006.01) |
| *A61K 39/00* | (2006.01) |
| *C07K 16/24* | (2006.01) |
| *C07K 16/28* | (2006.01) |
| *A61K 45/06* | (2006.01) |
| *C07K 16/30* | (2006.01) |
| *A61P 35/00* | (2006.01) |

(52) U.S. Cl.
CPC .......... *C07K 16/243* (2013.01); *A61K 39/395* (2013.01); *A61K 39/39558* (2013.01); *A61K 45/06* (2013.01); *A61P 35/00* (2018.01); *C07K 16/2803* (2013.01); *C07K 16/2818* (2013.01); *C07K 16/303* (2013.01); *C07K 16/3015* (2013.01); *C07K 16/3023* (2013.01); *C07K 16/3038* (2013.01); *C07K 16/3053* (2013.01); *C07K 16/3061* (2013.01); *C07K 16/3069* (2013.01); *A61K 39/3955* (2013.01); *A61K 39/39533* (2013.01); *A61K 2039/507* (2013.01); *C07K 2317/56* (2013.01); *C07K 2317/565* (2013.01)

(58) Field of Classification Search
None
See application file for complete search history.

(56) References Cited

U.S. PATENT DOCUMENTS

2015/0210769 A1 * 7/2015 Freeman ............ C07K 16/2896
424/136.1

FOREIGN PATENT DOCUMENTS

| WO | WO 2005/068503 A2 * | 7/2005 |
|---|---|---|
| WO | 2015026684 A1 | 2/2015 |
| WO | 2015036511 A1 | 3/2015 |
| WO | 2015112900 A1 | 7/2015 |

OTHER PUBLICATIONS

Zhu et al., "CSF1/CSF1R blockade reprograms tumor-infiltrating macrophages and improves response to T-cell checkpoint immunotherapy in pancreatic cancer models", Cancer Research, 2014, vol. 74, No. 18, pp. 5057-5069.

* cited by examiner

*Primary Examiner* — Elizabeth C. Kemmerer
(74) *Attorney, Agent, or Firm* — Natasha Iyer; Novartis AG

(57) ABSTRACT

The present application n relates to a pharmaceutical composition comprising a PD-1 antibody and an M-CSF antibody. The combination can be administered independently or separately, in a quantity which is therapeutically effective for the treatment of cancer.

9 Claims, 1 Drawing Sheet
Specification includes a Sequence Listing.

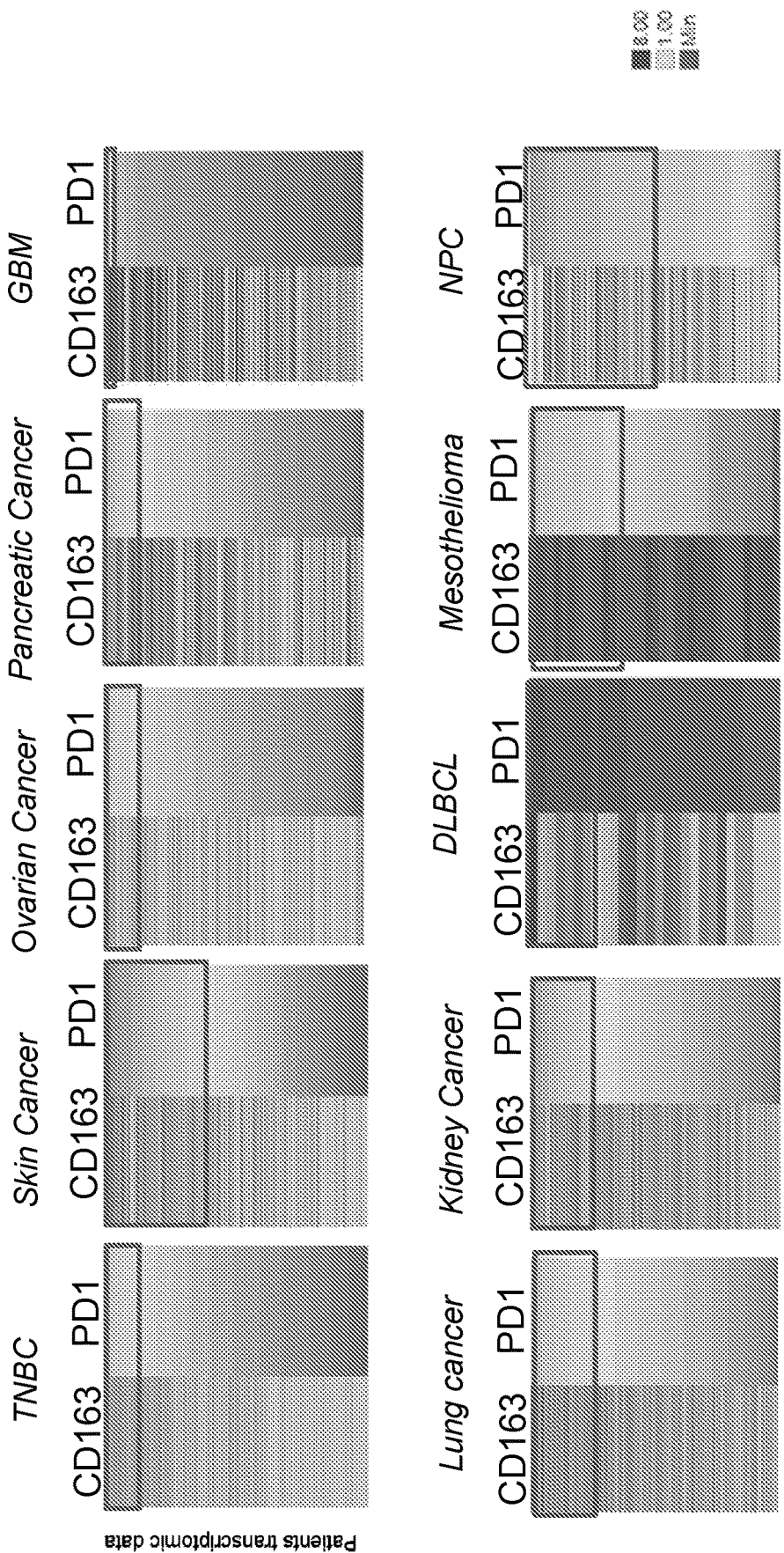

SEQUENCE LISTING

```
<160> NUMBER OF SEQ ID NOS: 48

<210> SEQ ID NO 1
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1
```

```
Gln Val Gln Leu Gln Glu Ser Gly Pro Gly Leu Val Lys Pro Ser Gln
1               5                   10                  15

Thr Leu Ser Leu Thr Cys Thr Val Ser Asp Tyr Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Gln Leu Asn Ser Val Thr Ala Ala Asp Thr Ala Val Tyr Tyr Cys
                85                  90                  95

Ala Ser Phe Asp Tyr Ala His Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445

<210> SEQ ID NO 2
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Asp Ile Val Leu Thr Gln Ser Pro Ala Phe Leu Ser Val Thr Pro Gly
1               5                   10                  15

Glu Lys Val Thr Phe Thr Cys Gln Ala Ser Gln Ser Ile Gly Thr Ser
            20                  25                  30

Ile His Trp Tyr Gln Gln Lys Thr Asp Gln Ala Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Ser Ser Val Glu Ala
65                  70                  75                  80

Glu Asp Ala Ala Asp Tyr Tyr Cys Gln Gln Ile Asn Ser Trp Pro Thr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ser Asp Tyr Ala Trp Asn
1               5

<210> SEQ ID NO 4
<211> LENGTH: 16
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Tyr Ile Ser Tyr Ser Gly Ser Thr Ser Tyr Asn Pro Ser Leu Lys Ser
1               5                   10                  15

<210> SEQ ID NO 5
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Phe Asp Tyr Ala His Ala Met Asp Tyr
1               5

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Ala Ser Gln Ser Ile Gly Thr Ser Ile His
1               5                   10

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Tyr Ala Ser Glu Ser Ile Ser
1               5

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln Gln Ile Asn Ser Trp Pro Thr Thr
1               5

<210> SEQ ID NO 9
<211> LENGTH: 467
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 9

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Gln Thr Leu Ser Leu Thr Cys Thr Val Ser Asp Tyr Ser Ile
        35                  40                  45

Thr Ser Asp Tyr Ala Trp Asn Trp Ile Arg Gln Phe Pro Gly Lys Gly
    50                  55                  60

Leu Glu Trp Met Gly Tyr Ile Ser Tyr Ser Gly Ser Thr Ser Tyr Asn
65                  70                  75                  80

Pro Ser Leu Lys Ser Arg Ile Thr Ile Ser Arg Asp Thr Ser Lys Asn
                85                  90                  95

Gln Phe Ser Leu Gln Leu Asn Ser Val Thr Ala Ala Asp Thr Ala Val
            100                 105                 110

Tyr Tyr Cys Ala Ser Phe Asp Tyr Ala His Ala Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400
```

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 10
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Val Ser Thr Pro Gln Phe Leu Val Phe Leu Leu Phe Trp Ile Pro
1               5                   10                  15

Ala Ser Arg Gly Asp Ile Val Leu Thr Gln Ser Pro Ala Phe Leu Ser
            20                  25                  30

Val Thr Pro Gly Glu Lys Val Thr Phe Thr Cys Gln Ala Ser Gln Ser
        35                  40                  45

Ile Gly Thr Ser Ile His Trp Tyr Gln Gln Lys Thr Asp Gln Ala Pro
    50                  55                  60

Lys Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Thr Ile Ser
                85                  90                  95

Ser Val Glu Ala Glu Asp Ala Ala Asp Tyr Tyr Cys Gln Gln Ile Asn
            100                 105                 110

Ser Trp Pro Thr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 11
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 11

Glu Val Gln Leu Val Gln Ser Gly Ala Glu Val Lys Pro Gly Glu
1               5                   10                  15

Ser Leu Arg Ile Ser Cys Lys Gly Ser Gly Tyr Thr Phe Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 12
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 13

Thr Tyr Trp Met His
1               5

```
<210> SEQ ID NO 14
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asn Ile Tyr Pro Gly Thr Gly Gly Ser Asn Phe Asp Glu Lys Phe Lys
1               5                   10                  15

Asn

<210> SEQ ID NO 15
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Trp Thr Thr Gly Thr Gly Ala Tyr
1               5

<210> SEQ ID NO 16
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Lys Ser Ser Gln Ser Leu Leu Asp Ser Gly Asn Gln Lys Asn Phe Leu
1               5                   10                  15

Thr

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Trp Ala Ser Thr Arg Glu Ser
1               5

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gln Asn Asp Tyr Ser Tyr Pro Tyr Thr
1               5
```

<210> SEQ ID NO 19
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
```

```
                355                 360                 365
Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 20
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic peptide"

<400> SEQUENCE: 21

Thr Tyr Trp Met His
1               5

<210> SEQ ID NO 22
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Asn Ile Tyr Pro Gly Thr Gly Gly Ser Asn Phe Asp Glu Lys Phe Lys
1               5                   10                  15

Asn

<210> SEQ ID NO 23
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Trp Thr Thr Gly Thr Gly Ala Tyr
1               5

<210> SEQ ID NO 24
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 25
<211> LENGTH: 443
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380
```

```
Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 26
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Lys Ser Ser Gln Ser Leu Leu Asp Ser Gly Asn Gln Lys Asn Phe Leu
1               5                   10                  15

Thr

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Trp Ala Ser Thr Arg Glu Ser
1               5

<210> SEQ ID NO 28
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gln Asn Asp Tyr Ser Tyr Pro Tyr Thr
1               5

<210> SEQ ID NO 29
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
```

```
                35                  40                  45
Ala Pro Arg Leu Leu Ile Tyr Trp Ala Ser Thr Arg Glu Ser Gly Val
             50                  55                  60
Pro Ser Arg Phe Ser Gly Ser Gly Ser Gly Thr Asp Phe Thr Phe Thr
 65                  70                  75                  80
Ile Ser Ser Leu Glu Ala Glu Asp Ala Ala Thr Tyr Tyr Cys Gln Asn
                 85                  90                  95
Asp Tyr Ser Tyr Pro Tyr Thr Phe Gly Gln Gly Thr Lys Val Glu Ile
                100                 105                 110
Lys
```

<210> SEQ ID NO 30
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

```
Glu Ile Val Leu Thr Gln Ser Pro Ala Thr Leu Ser Leu Ser Pro Gly
 1               5                  10                  15
Glu Arg Ala Thr Leu Ser Cys Lys Ser Ser Gln Ser Leu Leu Asp Ser
             20                  25                  30
Gly Asn Gln Lys Asn Phe Leu Thr Trp Tyr Gln Gln Lys Pro Gly Gln
         35                  40                  45
Ala Pro Arg Leu Leu Ile Tyr Trp Ala Ser Thr Arg Glu Ser Gly Val
     50                  55                  60
Pro Ser Arg Phe Ser Gly Ser Gly Ser Gly Thr Asp Phe Thr Phe Thr
 65                  70                  75                  80
Ile Ser Ser Leu Glu Ala Glu Asp Ala Ala Thr Tyr Tyr Cys Gln Asn
                 85                  90                  95
Asp Tyr Ser Tyr Pro Tyr Thr Phe Gly Gln Gly Thr Lys Val Glu Ile
                100                 105                 110
Lys Arg Thr Val Ala Ala Pro Ser Val Phe Ile Phe Pro Pro Ser Asp
            115                 120                 125
Glu Gln Leu Lys Ser Gly Thr Ala Ser Val Val Cys Leu Leu Asn Asn
        130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
    210                 215                 220
```

<210> SEQ ID NO 31
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Met Ala Trp Val Trp Thr Leu Pro Phe Leu Met Ala Ala Ala Gln Ser
1               5                   10                  15

Val Gln Ala

<210> SEQ ID NO 32
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Met Ser Val Leu Thr Gln Val Leu Ala Leu Leu Leu Leu Trp Leu Thr
1               5                   10                  15

Gly Thr Arg Cys
            20

<210> SEQ ID NO 33
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Met Ala Trp Val Trp Thr Leu Pro Phe Leu Met Ala Ala Ala Gln Ser
1               5                   10                  15

Val Gln Ala

<210> SEQ ID NO 34
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Met Ser Val Leu Thr Gln Val Leu Ala Leu Leu Leu Leu Trp Leu Thr
1               5                   10                  15

Gly Thr Arg Cys
            20

<210> SEQ ID NO 35
<211> LENGTH: 327
<212> TYPE: PRT
<213> ORGANISM: Homo sapiens

<400> SEQUENCE: 35

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 36
<211> LENGTH: 107
<212> TYPE: PRT
<213> ORGANISM: Homo sapiens

<400> SEQUENCE: 36

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

```
Pro Val Thr Lys Ser Phe Asn Arg Gly Glu Cys
            100                 105
```

<210> SEQ ID NO 37
<211> LENGTH: 326
<212> TYPE: PRT
<213> ORGANISM: Homo sapiens
<400> SEQUENCE: 37

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325
```

<210> SEQ ID NO 38
<211> LENGTH: 330
<212> TYPE: PRT
<213> ORGANISM: Homo sapiens

<400> SEQUENCE: 38

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 39
<211> LENGTH: 330
<212> TYPE: PRT
<213> ORGANISM: Homo sapiens

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 40
<211> LENGTH: 330
<212> TYPE: PRT
<213> ORGANISM: Homo sapiens

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                100                 105                 110

Pro Ala Pro Glu Leu Leu Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 330
<212> TYPE: PRT
<213> ORGANISM: Homo sapiens

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 42
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Arg Phe Arg Asp Asn Thr Pro Asn
1               5

<210> SEQ ID NO 43
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Arg Phe Arg Asp Asn Thr Ala Asn
1               5

<210> SEQ ID NO 44
<211> LENGTH: 9
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 44

Ile Thr Phe Glu Phe Val Asp Gln Glu
1               5

<210> SEQ ID NO 45
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Trp Gly Gln Gly Thr Thr Val Thr Val Ser Ser
1               5                   10

<210> SEQ ID NO 46
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Phe Gly Gln Gly Thr Lys Val Glu Ile Lys
1               5                   10

<210> SEQ ID NO 47
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
gctgacagac taacagactg ttcc                                          24

<210> SEQ ID NO 48
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
caaatgtggt atggctga                                                 18
```

COMBINED USE OF ANTI PD-1 AND ANTI M-CSF ANTIBODIES IN THE TREATMENT OF CANCER

CROSS REFERENCE TO RELATED APPLICATIONS

This application is a national stage application under 35 U.S.C § 371 of International Application No. PCT/162016/054487 filed Jul. 27, 2016, which claims priority under 35 U.S.C § 119(e) to U.S. Provisional Application No. 62/352,637 filed Jun. 21, 2016 and U.S. Provisional Application No. 62/198,384 filed Jul. 29, 2015, the contents of each of which are incorporated herein by reference in their entirety.

FIELD OF THE INVENTION

The present invention relates, in part, to a pharmaceutical composition comprising a PD-1 antagonist and an M-CSF antagonist. The present combination is administered independently or separately, in a quantity which is therapeutically effective for the treatment of cancer. The invention further relates to a use of such a combination for the manufacture of a medicament; the use of such combination as a medicine; a kit of parts comprising such a combination; and a method of treatment involving the combination.

BACKGROUND OF THE INVENTION

More effective treatments for cancer solid tumors are needed. Immunotherapies that target immune checkpoints are currently emerging as key agents in cancer therapy. Antibodies inhibiting cytotoxic T-lymphocyte-associated protein 4 (CTLA-4) and programmed death-1 (PD-1), also known as checkpoint inhibitors, have demonstrated effectiveness in some cancer patients. Patients and tumor types have had strongly varying responses, with highest rates of response observed in advanced melanoma. Both non-responsiveness to checkpoint inhibition as well as initial response followed by progression have been observed, indicating the presence of intrinsic resistance and therapy-induced acquired resistance. Melanoma patients whose disease progresses on CTLA-4, PD-1 or PD-L1 checkpoint inhibitors are in need of other treatment options that can stabilize or reverse disease progression.

One cancer that may benefit from treatment with a checkpoint inhibiting antibody is breast cancer, the most common cancer among women worldwide, with an estimated 1.38 million new cases in 2008, and it is also the most common cause of cancer death in women with 458,000 deaths. Triple-negative breast cancer (TNBC) accounts for approximately 15% of newly diagnosed breast cancers, but due to its aggressive nature a disproportionate number (25%) of TNBC are reported in the metastatic setting. TNBC is characterized by lack of expression of the estrogen (ER) and progesterone (PR) receptors and lack of overexpression of the human epidermal growth factor receptor 2 (HER2).

The clinical course of TNBC is associated with a high probability of distant metastases, especially to the lung and brain. Currently, there are no targeted therapies for this breast cancer subtype and the only treatment option is chemotherapy. Even though several studies suggest that TNBC is a highly chemosensitive disease, prognosis still remains poor with a shorter disease free interval after initial therapy and a more aggressive clinical course in the metastatic setting. Most patients receive anthracyclines and taxanes in the adjuvant setting and no further standard of care therapy exists for patients with metastatic TNBC. However, emerging data suggest that platinum salts (ie, cisplatin and carboplatin) are highly active in early and advanced TNBC, and therefore widely used in the clinical setting. Median survival for metastatic TNBC is approximately 1 year, making TNBC a disease with high unmet medical need. Additional cancers with high unmet patient needs also include patients with pancreatic cancer (especially patients with pancreatic adenocarcinoma) or endometrial carcinoma. There exists a need for developing novel combination therapies that can be used to treat cancer.

SUMMARY OF THE INVENTION

The present invention is directed, in part, to a combination of a macrophage colony stimulating factor (M-CSF) antagonist and a Programmed Death 1 (PD-1) antagonist that can provide an advantageous effect for treatment of cancer. The M-CSF antagonist and PD-1 antagonist combination is used in the treatment of cancer including triple negative breast cancer (TNBC), skin, ovarian, pancreatic cancers, glioblastoma (GBM), lung cancer, kidney renal cell carcinoma, diffuse large b cell lymphoma (DLBCL), mesothelioma, endometrial cancer and nasopharylngeal carcinoma (NPC), or a cancer that has become resistant or refractory to PD-1 or PD-L1 therapy such as TNBC or melanoma.

In another aspect, the invention includes the pharmaceutical combination described above for use in the treatment of cancer including triple negative breast cancer (TNBC), skin, ovarian, pancreatic cancers, glioblastoma (GBM), lung cancer, kidney renal cell carcinoma, diffuse large b cell lymphoma (DLBCL), mesothelioma, and nasopharylngeal carcinoma (NPC), or a cancer that has become resistant, relapsing or refractory to other therapies, especially to PD-1 or PD-L1 therapy such as TNBC or melanoma. The combination of the invention can be used to treat lung cancer including non-small lung cancer and squamous cell lung cancer. The pharmaceutical combination described herein includes a quantity which is therapeutically effective. Breast cancers include endocrine receptor (estrogen or progesterone receptor) positive, HER2 positive, triple negative (not positive to receptors for estrogen, progesterone, or HER2) or triple positive (positive for estrogen receptors, progesterone receptors and HER2) and the combination of the present invention is especially useful against triple negative breast cancer. Pancreatic cancers are mostly of the adenocarcinoma or carcinoma type, which are exocrine cancers. Pancreatic exocrine cancers include pancreatic adenocarcinoma, acinar cell carcinoma of the pancreas, cystadenocarcinomas, pancreatoblastoma adenosquamous carcinomas, signet ring cell carcinomas, hepatoid carcinomas, colloid carcinomas, undifferentiated carcinomas, undifferentiated carcinomas with osteoclast-like giant cells. solid pseudopapillary tumor and pancreatic mucinous cystic neoplasms.

In one embodiment, the pharmaceutical combination described herein includes a quantity which is therapeutically effective for the treatment of breast cancer such as endocrine receptor (estrogen or progesterone receptor) positive, HER2 positive, triple negative (not positive to receptors for estrogen, progesterone, or HER2) or triple positive (positive for estrogen receptors, progesterone receptors and HER2). In another embodiment, the pharmaceutical combination described herein includes a quantity which is therapeutically effective for the treatment of ovarian cancer. In yet another embodiment, the pharmaceutical combination described herein includes a quantity which is therapeutically effective for the treatment of melanoma including melanoma. In still yet another embodiment, the pharmaceutical combination described herein includes a quantity which is therapeutically effective for the treatment of pancreatic cancer. In still yet another embodiment, the pharmaceutical combination described herein includes a quantity which is therapeutically effective for the treatment of lung cancer including non-small lung cancer and squamous cell lung cancer. In another embodiment, the pharmaceutical combination described herein includes a quantity which is therapeutically effective for the treatment of a cancer that has become resistant or refractory to PD-1 or PD-L1 therapy such as TNBC or melanoma. In still yet another embodiment, the pharmaceutical combination described herein includes a quantity which is therapeutically effective for the treatment of In another aspect, the invention includes the pharmaceutical combination described herein for use in the treatment of a cancer such as breast cancer including triple negative breast cancer (TNBC), skin, ovarian, pancreatic cancers, glioblastoma (GBM), lung cancer, kidney renal cell carcinoma, diffuse large b cell lymphoma (DLBCL), mesothelioma, and nasopharylngeal carcinoma (NPC), or a cancer that has become resistant or refractory to PD-1 or PD-L1 therapy such as TNBC or melanoma.

In another aspect, the invention includes use of the pharmaceutical combination described herein for the manufacture of a medicament for treatment of a cancer such as breast cancer including triple negative breast cancer (TNBC), skin, ovarian, pancreatic cancers, glioblastoma (GBM), lung cancer, kidney renal cell carcinoma, diffuse large b cell lymphoma (DLBCL), mesothelioma, and nasopharylngeal carcinoma (NPC), or a cancer that has become resistant or refractory to PD-1 or PD-L1 therapy such as TNBC or melanoma.

BRIEF DESCRIPTION OF FIGURES

FIG. 1 shows Rnaseq data from the TCGA and internal databases showing high level of expression of the surrogate marker for M2 macrophages, CD163, within particular patient populations defined by the highest level of PD1 expression (box).

SPECIFIC DESCRIPTION OF THE INVENTION

There exists a need for novel combinations that can be used to treat cancer. The present invention is directed to a combination of an M-CSF antagonist, such as an anti-M-CSF antibody molecule, and a PD-1 antagonist, such as an anti-PD-1 antibody molecule, that can be used to treat cancers. While not wishing to be bound by theory the use of the novel combination disclosed herein to treat a particular cancer is believed to be advantageous as it affects the immune response rescuing T cell antitumor response and expanding the endogenous antitumor response of T cells. As shown in FIG. 1, after activation, T cells increase the expression of PD-1 on their surface, allowing them to receive a negative signal thereby inhibiting T cell responses. Tumor cells have taken advantage of this system by expressing binding partners of PD-1, such as PD-L1 that prematurely shut down T cell responses against the tumor. In the present combination, the anti-PD1 antibody molecule recognizes and binds PD-1 on T cells thereby preventing the tumor cells from binding PD-1 and reducing T cell activity. The anti-PD-1 antibody molecule binds the T cell but does not interfere with T cell function thus ensuring that cells retain their tumor killing affect. The anti-M-CSF antibody in turn augments T cell activity by affecting a different cellular axis. At the site of the tumor, tumor associated macrophages (TAMS) secrete cytokines to inhibit IL-2 production and proliferation of T cells in a paracrine manner. The use of the anti-M-CSF antibody releases the break from the T cell compartment by depleting M2 macrophages which can suppress T cell function and proliferation through the production of immunomodulatory cytokines. Thus the combination of an anti-MSCF antibody molecule and anti-PD1 antibody molecule is believed to rescue the function of exhausted T cells which has been impaired by tumor cells and M2 macrophages leading to an advantageous treatment affect in patients with tumors. The presently novel combinations can be useful in indications where a PD-1 marker and CD163 (a macrophage marker) are expressed or overexpressed. Examples of cancers where the combination has an advantageous affect include ovarian cancer, breast cancer, e.g., TNBC, pancreatic cancer, melanoma, lung cancer such as non-small lung cancer and squamous cell lung cancer, nasopharyngeal carcinoma (NPC), diffuse large b cell lymphoma (DLBCL), mesothelioma, kidney renal cell carcinoma, or glioblastoma. Moreover, the present combinations are useful to treat cancers that are resistant or refractory to PD1/PDL-1 treatment including melanoma and triple negative breast cancer (TNBC).

Thus, the present invention provides, compositions, e.g., pharmaceutical compositions, which include a pharmaceutically acceptable carrier, excipient or stabilizer, and the anti-PD-1 antibody molecule described herein and an anti-M-CSF antibody as described herein and uses thereof to treat cancer. In one embodiment, the composition, e.g., the pharmaceutical composition includes a combination of the anti-PD-1 and anti-M-CSF antibody molecules and one or more agents, e.g., a therapeutic agent or other antibody molecule, as described herein.

Definitions

The term "Programmed Death 1" or "PD-1" include isoforms, mammalian, e.g., human PD-1, species homologs of human PD-1, and analogs comprising at least one common epitope with PD-1. The amino acid sequence of PD-1, e.g., human PD-1, is known in the art, e.g., Shinohara T et al. (1994) Genomics 23(3):704-6; Finger L R, et al. Gene (1997) 197(1-2):177-87.

The term "jointly therapeutically effective" means that the PD-1 antagonist e.g., the anti PD-1 antibody molecule and the M-CSF antagonist, e.g., the anti M-CSF antibody molecule may be given simultaneously (in one dosage form or multiple dosage forms) or separately (in a chronologically staggered manner, especially a sequence-specific manner) in such time intervals that they prefer, in the subject, especially human, to be treated, and still show a (preferably an improved or synergistic) interaction. In one embodiment, the combination when administered shows an improved therapeutic response when compared to therapeutic response when administered as a monotherapy to a subject with cancer.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The compositions and methods of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

The term "antigen-binding site" refers to the part of an antibody molecule that comprises determinants that form an interface that binds to the PD-1 or M-CSF polypeptide, or an epitope thereof. With respect to proteins (or protein mimetics), the antigen-binding site typically includes one or more loops (of at least four amino acids or amino acid mimics) that form an interface that binds to the or M-CSF PD-1 polypeptide. Typically, the antigen-binding site of an antibody molecule includes at least one or two CDRs and/or hypervariable loops, or more typically at least three, four, five or six CDRs and/or hypervariable loops.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response.

"Combination" refers to formulations of the separate partners with or without instructions for combined use or to combination products. The combination partners may thus be entirely separate pharmaceutical dosage forms or pharmaceutical compositions that are also sold independently of each other and where just instructions for their combined use are provided in the package equipment, e.g. leaflet or the like, or in other information e.g. provided to physicians and medical staff (e.g. oral communications, communications in writing or the like), for simultaneous or sequential use for being jointly active.

"Combination product" includes a kit of parts for the combined administration where an anti-PD-1 antibody and an anti M-CSF antibody may be administered independently at the same time or separately within time intervals, especially where these time intervals allow that the combination partners show a cooperative (=joint), e.g. improved, enhanced or synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration and/or at the same time.

The term "non-fixed combination" means that the active ingredients are both administered to a patient as separate entities either simultaneously, concurrently or sequentially with no specific time limits, wherein such administration provides therapeutically effective levels of the two antibodies in the body of the patient. The latter also applies to cocktail therapy, e.g. the administration of three or more active ingredients. The term "non-fixed combination" thus defines especially a "kit of parts" in the sense that the combination partners (i) an anti-PD-1 antibody and (ii) an anti M-CSF antibody as defined herein can be dosed independently of each other or by use of different fixed combinations with distinguished amounts of the combination partners, i.e. simultaneously or at different time points, where the combination partners may also be used as entirely separate pharmaceutical dosage forms or pharmaceutical formulations that are also sold independently of each other and just instructions of the possibility of their combined use is or are provided in the package equipment, e.g. leaflet or the like, or in other information e.g. provided to physicians and medical staff. The independent formulations or the parts of the kit of parts can then, e.g. be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (i) and (ii), thus being jointly active. The ratio of the total amounts of the combination partner (i) to the combination partner (ii) to be administered in the combined preparation can be varied, e.g. in order to cope with the needs of a patient sub-population to be treated or the needs of the single patient which different needs can be due to age, sex, body weight, etc. of the patients.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "antibody molecule" refers to a protein, e.g., an immunoglobulin chain or fragment thereof, comprising at least one immunoglobulin variable domain sequence. The term "antibody molecule" includes, for example, a monoclonal antibody (including a full length antibody which has an immunoglobulin Fc region). In an embodiment, an antibody molecule comprises a full length antibody, or a full length immunoglobulin chain. In an embodiment, an antibody molecule comprises an antigen binding or functional fragment of a full length antibody, or a full length immunoglobulin chain. In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The a preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv); (viii) a single domain antibody. These antibody fragments are obtained using conventional techniques known to those with skill in the art, and the fragments are screened for utility in the same manner as are intact antibodies. The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273, 927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

Generally, unless specifically indicated, the anti-PD-1 antibody molecules can include any combination of one or more Kabat CDRs and/or Chothia hypervariable loops, e.g., described in Table 2. In one embodiment, the following definitions are used for the anti-PD-1 antibody molecules described in Table 2: HCDR1 according to the combined CDR definitions of both Kabat and Chothia, and HCCDRs 2-3 and LCCDRs 1-3 according the CDR definition of Kabat. Under all definitions, each VH and VL typically includes three CDRs and four FRs, arranged from amino-terminus to carboxy-terminus in the following order: FR1, CDR1, FR2, CDR2, FR3, CDR3, FR4.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule, In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope. In an embodiment the first epitope is located on PD-1 and the second epitope is located on a TIM-3, LAG-3, CEACAM (e.g., CEACAM-1 and/or CEACAM-5), PD-L1, or PD-L2.

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to PD-1. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences. In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

The pharmaceutical compositions of the invention may include a "therapeutically effective amount" or a "prophylactically effective amount" of an antibody or antibody portion of the invention. A "therapeutically effective amount" or "jointly therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by therapeutically beneficial effects. A therapeutically effective dosage of the disclosed combination preferably inhibits a measurable parameter, e.g., tumor growth rate by at least about 20%, more preferably by at least about 40%, even more preferably by at least about 60%, and still more preferably by at least about 80% relative to untreated subjects. The ability of the combination disclosed herein to inhibit a measurable parameter, e.g., cancer, can be evaluated in a clinical trial and evaluated by a skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than therapeutically effective amount.

Also within the scope of the invention is a kit comprising an anti-PD-1 antibody molecule and an anti-M-CSF antibody molecule as described herein. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

SEQUENCE LISTING

The instant application contains a Sequence Listing which has been submitted electronically in ASCII format and is hereby incorporated by reference in its entirety. Said ASCII copy, created on Jul. 11, 2016, is named PAT057000_SL.txt and is 55,243 bytes in size.

Examples of Macrophage Colony Stimulating Factor (M-CSF) Antibody Antagonists

The various forms of M-CSF as described below function by binding to its receptor (M-CSFR) on target cells. M-CSFR is a membrane spanning molecule with five extracellular immunoglobulin-like domains, a transmembrane domain and an intracellular interrupted Src related tyrosine kinase domain. M-CSFR is encoded by the c-fms proto-oncogene. Binding of M-CSF to the extracellular domain of M-CSFR leads to dimerization of the receptor, which activates the cytoplasmic kinase domain, leading to autophosphorylation and phosphorylation of other cellular proteins (Hamilton J. A., J Leukoc Biol., 62(2):145-55 (1997); Hamilton J, A., Immuno Today., 18(7): 313-7(1997).

The full-length human M-CSF (also known as Colony stimulating factor (CSF-1)) mRNA encodes a precursor protein of 554 amino acids. Through alternative mRNA splicing and differential post-translational proteolytic processing, M-CSF can either be secreted into the circulation as a glycoprotein or chondroitin sulfate containing proteoglycan or be expressed as a membrane spanning glycoprotein on the surface of M-CSF producing cells. The three-dimensional structure of the bacterially expressed amino terminal 150 amino acids of human M-CSF, the minimal sequence required for full in vitro biological activity, indicates that this protein is a disulfide linked dimer with each monomer consisting of four alpha helical bundles and an anti-parallel beta sheet (Pandit et al., Science 258: 1358-62 (1992)). Three distinct M-CSF species are produced through alternative mRNA splicing. The three polypeptide precursors are M-CFSα of 256 amino acids, M-CSFβ of 554 amino acids, and M-CSFγ of 438 amino acids. M-CSFβ is a secreted protein that does not occur in a membrane-bound form. M-CSFα is expressed as an integral membrane protein that is slowly released by proteolytic cleavage. M-CSFα is cleaved at amino acids 191-197. The membrane-bound form of M-CSF can interact with receptors on nearby cells and therefore mediates specific cell-to-cell contacts. The term "M-CSF" may also include amino acids 36-438.

M-CSF antagonists have been described. The M-CSF antagonist of the combination can be a small molecule, an antibody or other antigen-binding protein, a small molecule, a nucleic acid (such as an siRNA), or any other such molecule which interferes with M-CSF activation or function.

In one example, the M-CSF antagonist is an anti M-CSF antibody molecule. Anti-M-CSF antibodies that can be useful in the present invention include those anti-M-CSF antibodies disclosed in Int'l Publication No. WO 2005/068503, which is hereby incorporated by reference in its entirety for its teaching with respect to M-CSF antibodies. WO 2005/068503 discloses, for example, antibodies that bind the same epitopes as antibodies RX1, 5H4, MC1, and/or MC3, pharmaceutical formulations including an anti-M-CSF-specific antibody Human Engineered™ versions of the aforementioned antibodies, and methods of preparing the pharmaceutical formulations. The term "antibody" is used in the broadest sense and includes fully assembled antibodies, monoclonal antibodies, polyclonal antibodies, multispecific antibodies (e.g., bispecific antibodies), antibody fragments that can bind antigen (e.g., Fab', F'(ab)2, Fv, single chain antibodies, diabodies), and recombinant peptides comprising the forgoing as long as they exhibit the desired biological activity.

Other anti-M-CSF antibodies that can be useful in the present invention include those M-CSF antibodies disclosed in Int'l Publication No. WO 2003/028752, US2009117103 and US2005059113, each of which is hereby incorporated by reference in its entirety for its teaching with respect to anti-M-CSF antibody molecules.

In one embodiment, the antibody molecule useful in the methods of the invention include an antibody molecule that binds to a linear epitope represented by RFRDNTPN (SEQ ID NO: 42) or RFRDNTAN (SEQ ID NO: 43). Such an antibody is the human engineered RX1 (H-RX1) antibody disclosed in WO 2005/068503. In another embodiment, the antibody can be an antibody molecule that binds to a linear epitope represented by ITFEFVDQE (SEQ ID NO: 44). Such an antibody is the 5H4 disclosed in WO 2005/068503.

In one embodiment, the H-RX1 is used in the combination of the invention. The heavy and light constant, variable regions, and complimentary determining regions (CDRs) of the H-RX1 antibody or an antigen binding fragment thereof are shown in Table 1.

TABLE 1

| H-RX1, an anti-M-CSF antibody | |
|---|---|
| (H-RX1) HC derived protein | QVQLQESGPGLVKPSQTLSLTCTVSDYSITSDYAWNWIRQFPGKG LEWMGYISYSGSTSYNPSLKSRITISRDTSKNQFSLQLNSVTAADT AVYYCASFDYAHAMDYVVGQGTTVTVSSASTKGPSVFPLAPSSKS TSGGTAALGCLVKDYFPEPVTVSWNSGALTSGVHTFPAVLQSSGL YSLSSVVTVPSSSLGTQTYICNVNEIKPSNTKVDKRVEPKSCDKTHT CPPCPAPELLGGPSVFLFPPKPKDTLMISRTPEVTCVVVDVSHEDPE VKFNWYVDGVEVHNAKTKPREEQYNSTYRVVSVLTVLHQDWLN GKEYKCKVSNKALPAPIEKTISKAKGQPREPQVYTLPPSREEMTKN QVSLTCLVKGFYPSDIAVEWESNGQPENNYKTTPPVLDSDGSFFLY SKLTVDKSRWQQGNVFSCSVMHEALHNHYTQKSLSLSPGK (SEQ ID NO: 1) |
| (H-RX1) LC derived protein | DIVLTQSPAFLSVTPGEKVTFTCQASQSIGTSIHVVYQQKTDQAPKL LIKYASESISGIPSRFSGSGSGTDFTLTISSVEAEDAADYYCQQINSW PTTFGGGTKLEIKRTVAAPSVFIFPPSDEQLKSGTASVVCLLNNFYP REAKVQWKVDNALQSGNSQESVTEQDSKDSTYSLSSTLTLSKAD YEKEIKVYACEVTHQGLSSPVTKSFNRGEC (SEQ ID NO: 2) |
| Heavy Chain CDR1 (Kabat) | SDYAWN (SEQ ID NO: 3) |
| Heavy Chain CDR2 (Kabat) | YISYSGSTSYNPSLKS (SEQ ID NO: 4) |
| Heavy Chain CDR3 (Kabat) | FDYAHAMDY (SEQ ID NO: 5) |
| Light Chain CDR1 (Kabat) | QASQSIGTSIH (SEQ ID NO: 6) |
| Light Chain CDR2 (Kabat) | YASESIS (SEQ ID NO: 7) |
| Light Chain CDR3 (Kabat) | QQINSWPTT (SEQ ID NO: 8) |

TABLE 1-continued

H-RX1, an anti-M-CSF antibody

| | |
|---|---|
| (H-RX 1) HC derived protein (incl. leader peptide) | MGWSCIILFLVATATGVHSQVQLQESGPGLVKPSQTLSLTCTVSDYSI<br>TSDYAWNWIRQFPGKGLEWMGYISYSGSTSYNPSLKSRITISRDTS<br>KNQFSLQLNSVTAADTAVYYCASFDYAHAMDYVVGQGTTVTVSS<br>ASTKGPSVFPLAPSSKSTSGGTAALGCLVKDYFPEPVTVSWNSGAL<br>TSGVHTFPAVLQSSGLYSLSSVVTVPSSSLGTQTYICNVNEIKPSNT<br>KVDKRVEPKSCDKTHTCPPCPAPELLGGPSVFLFPPKPKDTLMISR<br>TPEVTCVVVDVSHEDPEVKFNVVYVDGVEVHNAKTKPREEQYNST<br>YRVVSVLTVLHQDWLNGKEYKCKVSNKALPAPIEKTISKAKGQPR<br>EPQVYTLPPSREEMTKNQVSLTCLVKGFYPSDIAVEWESNGQPEN<br>NYKTTPPVLDSDGSFFLYSKLTVDKSRWQQGNVFSCSVMHEALH<br>NHYTQKSLSLSPGK (SEQ ID NO: 9) |
| (H-RX1) LC derived protein (including leader peptide) | MVSTPQFLVFLLFWIPASRGDIVLTQSPAFLSVTPGEKVTFTCQASQS<br>IGTSIHVVYQQKTDQAPKLLIKYASESISGIPSRFSGSGSGTDFTLTISS<br>VEAEDAADYYCQQINSWPTTFGGGTKLEIKRTVAAPSVFIFPPSDE<br>QLKSGTASVVCLLNNFYPREAKVQWKVDNALQSGNSQESVIEQD<br>SKDSTYSLSSTLTLSKADYEKEIKVYACEVTHQGLSSPVTKSFNRG<br>EC (SEQ ID NO: 10) |

In one embodiment, the M-CSF antagonist antibody is a humanized antibody molecule having the heavy chain variable region sequence set forth in SEQ ID NO: 1 and light chain variable region sequence set forth in SEQ ID NO: 2. In another embodiment, the antibody molecule comprises a heavy chain variable region that comprises CDR1, CDR2, and CDR3 domains; and a light chain variable region that comprises CDR1, CDR2, and CDR3 domains, wherein the heavy chain variable region CDR3 comprises the amino acids having the sequence set forth in SEQ ID NO:5; and a light chain variable region CDR3 comprises amino acids having the sequence set forth in SEQ ID NO:8; and wherein the antibody or antigen-binding portion thereof binds to human M-CSF with a binding affinity of about $10^{-7}$ M. The antibody or fragment thereof can further include a heavy chain variable region CDR2 comprising amino acids having the sequence set forth in SEQ ID No: 4; and a light chain variable region CDR2 comprising amino acids having the sequence set forth in SEQ ID NO:7. The antibody or fragment thereof can further include a heavy chain variable region CDR1 comprising amino acids having the sequence set forth in SEQ ID NO:3; and a light chain variable region CDR1 comprising amino acids having the sequence set forth in SEQ ID NO:6.

In yet another example, the humanized antibody or human engineered antibody or fragment thereof useful in the methods of the invention binds to human M-CSF, wherein said antibody binds an epitope of M-CSF that comprises at least 4 contiguous residues of RFRDNTPN (SEQ ID NO: 42) or RFRDNTAN (SEQ ID NO: 43), wherein said antibody has an affinity Kd (dissociation equilibrium constant) with respect to human M-CSF of at least $10^{-7}$ M, wherein said antibody comprises all three heavy chain CDRs as specific above.

The antibodies disclosed herein can be derivatives of single chain antibodies, diabodies, domain antibodies, nanobodies, and unibodies. For example, the invention provides an isolated monoclonal antibody (or a functional fragment thereof) comprising a heavy chain variable region and a light chain variable region, wherein the heavy chain variable region comprises an amino acid sequence that is at least 80%, at least 90%, or at least 95% identical to an amino acid sequence of SEQ ID NOs: 1; the light chain variable region comprises an amino acid sequence that is at least 80%, at least 90%, or at least 95% identical to an amino acid sequence of SEQ ID NO:2; the antibody binds to M-CSF (e.g., human and/or cynomologus M-CSF) and neutralizes the signaling activity of M-CSF. when compared with the variable regions depicted in the sequence described above.

In other embodiments, the variable heavy chain (VH) and/or variable light chain (VL) amino acid sequences may be 50%, 60%, 70%, 80%, 90%, 95%, 96%, 97%, 98% or 99% identical to the sequences set forth in Table 1 above.

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the M-CSF-binding antibodies described in Table 1.

Accordingly, the invention provides an isolated M-CSF monoclonal antibody, or a fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequence includes SEQ ID NOs: 3, and conservative modifications thereof; the heavy chain variable region CDR2 amino acid sequences includes SEQ ID NOs: 4 and conservative modifications thereof; the heavy chain variable region CDR3 amino acid sequences includes SEQ ID NOs: 5 and conservative modifications thereof; the light chain variable regions CDR1 amino acid sequence includes SEQ ID NOs: 6 and conservative modifications thereof; the light chain variable regions CDR2 amino acid sequences includes SEQ ID NOs: 7, and conservative modifications thereof; the light chain variable regions of CDR3 amino acid sequence includes SEQ ID NOs: 8, and conservative modifications thereof; the antibody molecule specifically binds to M-CSF, and neutralizes M-CSF activity.

The antibodies used in the invention can be fragment of an antibody that binds to M-CSF selected from the group consisting of; Fab, F(ab$_2$)', F(ab)$_2$', scFv, VHH, VH, VL, dAbs. Methods of producing M-CSF antibodies are described in WO 2005/068503.

Examples of Antibody PD-1 Antagonists

The PD-1 molecules useful in the present invention can be any PD-1 antagonists. In one example, the PD-1 antagonist molecule such as an anti-PD-1 antibody molecule can inhibit, reduce or neutralize one or more activities of PD-1, resulting in blockade or reduction of an immune checkpoint. In one embodiment, the PD-1 antagonist molecule such as an anti-PD-1 antibody results in one or more of: an increase in tumor infiltrating lymphocytes, an increase in T-cell receptor mediated proliferation, a decrease in immune evasion by cancerous cells, restoration of effector cell function (e.g., one or more of T cell proliferation, IFN-alpha secretion or cytolytic function), inhibition of regulatory T cell function, or an effect on the activity of multiple cell types, such as regulatory T cell, effector T cells and NK cells).

The PD-1 molecules useful in the present invention are shown in Table 1 and as described in PCT application PCT/US2015/012754, which is incorporated herein in its entirety by reference.

In one embodiment, the anti-PD-1 antibody molecule is a humanized anti-PD-1 antibody and includes a heavy chain variable domain and a constant region, a light chain variable domain and a constant region, or both, comprising the amino acid sequence of BAP049-Clone-B or BAP049-Clone-E as described in Table 2, or encoded by the nucleotide sequence in Table 2 The anti-PD-1 antibody molecule, optionally, comprises a leader sequence from a heavy chain, a light chain, or both, as shown in Table 3; or a sequence substantially identical thereto.

In yet another embodiment, the anti-PD-1 antibody molecule includes at least one, two, or three complementarity determining regions (CDRs) from a heavy chain variable region of an antibody described herein, e.g., an antibody chosen from any of BAP049-Clone-B or BAP049-Clone-E as described in Table 2, or encoded by the nucleotide sequence in Table 2.

In an embodiment, e.g., an embodiment comprising a variable region, a CDR (e.g., Chothia CDR or Kabat CDR), or other sequence referred to herein, e.g., in Table 2, the antibody molecule is a monospecific antibody molecule, a bispecific antibody molecule, or is an antibody molecule that comprises an antigen binding fragment of an antibody, e.g., a half antibody or antigen binding fragment of a half antibody.

TABLE 2

PD-1 antibody heavy chain and light chain, CDRs and heavy chain and light chain variable domains

| BAP049-Clone-B | | | |
|---|---|---|---|
| SEQ ID NO: 11 | | VH | EVQLVQSGAEVKKPGESLRISCKGSGYTFTTYWMHWVRQATGQGLEWMGNIYPGTGGSNEDEKEKNRVTITADKSTSTAYMELSSLRSEDTAVYYCTRWTTGTGAYWGQGTTVTVSS |
| SEQ ID NO: 12 | | VL | EIVLTQSPATLSLSPGERATLSCKSQSLLDSGNQKNFLTWYQQKPGKAPKLLIYWASTRESGVPSRESGSGSGTDETFTISSLQPEDIATYYCQNDYSYPYTFGQGTKVEIK |
| SEQ ID NO: 13 | (Kabat) | HCDR1 | TYWMH |
| SEQ ID NO: 14 | (Kabat) | HCDR2 | NIYPGTGGSNEDEKEKN |
| SEQ ID NO: 15 | (Kabat) | HCDR3 | WTTGTGAY |
| SEQ ID NO: 16 | (Kabat) | LCDR1 | KSSQSLLDSGNQKNFLT |
| SEQ ID NO: 17 | (Kabat) | LCDR2 | WASTRES |
| SEQ ID NO: 18 | (Kabat) | LCDR3 | QNDYSYPYT |
| SEQ ID NO: 19 | | HC | EVQLVQSGAEVKKPGESLRISCKGSGYTETTYWMHWVRQATGQGLEWMGNIYPGTGGSNEDEKEKNRVTITADKSTSTAYMELSSLRSEDTAVYYCTRWTTGTGAYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDEIKPSNTKVDKRVESKYGPPCPPCPAPEELGGPSVELFPPKPKDTLMISRTPEVTCVVVDVSQEDPEVQFNWYVDGVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| SEQ ID NO: 20 | | LC | EIVLTQSPATLSLSPGERATLSCKSSQSLLDSGNQKNFLTWYQQKPGKAPKLLIYWASTRESGVPSRFSGSGSGTDFTFTISSLQPEDIATYYCQNDYSYPYTFGQGTKVEIKRTVAAPSVFIFPPSDEQLKSGTASVVCLLNNFYPREAKVQWKV |

TABLE 2-continued

PD-1 antibody heavy chain and light chain,
CDRs and heavy chain and light chain variable domains

|  |  |  |
|---|---|---|
|  |  | DNALQSGNSQESVTEQDSKDSTYSLS STLTLSKADYEKEIKVYACEVTHQGL SSPVTKSFNRGEC |
| BAP049-Clone-E HC |  |  |
| SEQ ID NO: 21 (Kabat) | HCDR1 | TYWMH |
| SEQ ID NO: 22 (Kabat) | HCDR2 | NIYPGTGGSNEDEKEKN |
| SEQ ID NO: 23 (Kabat) | HCDR3 | WTTGTGAY |
| SEQ ID NO: 24 | VH | EVQLVQSGAEVKKPGESLRISCKGSG YTFTTYWMHWVRQATGQGLEWMG NIYPGTGGSNEDEKEKNRVTITADKS TSTAYMELSSLRSEDTAVYYCTRWT TGTGAYWGQGTTVTVSS |
| SEQ ID NO: 25 | HC | EVQLVQSGAEVKKPGESLRISCKGSG YTFTTYWMHWVRQATGQGLEWMG NIYPGTGGSNEDEKEKNRVTITADKS TSTAYMELSSLRSEDTAVYYCTRWT TGTGAYWGQGTTVTVSSASTKGPSV FPLAPCSRSTSESTAALGCLVKDYFP EPVTVSWNSGALTSGVHTFPAVLQS SGLYSLSSVVTVPSSSLGTKTYTCNV DEIKPSNTKVDKRVESKYGPPCPPCP APEFLGGPSVFLFPPKPKDTLMISRTP EVTCVVVDVSQEDPEVQFNWYVDG VEVHNAKTKPREEQFNSTYRVVSVL TVLHQDWLNGKEYKCKVSNKGLPS SIEKTISKAKGQPREPQVYTLPPSQEE MTKNQVSLTCLVKGFYPSDIAVEWE SNGQPENNYKTTPPVLDSDGSFFLYS RLTVDKSRWQEGNVFSCSVMHEAL HNHYTQKSLSLSLG |
| BAP049-Clone-E LC |  |  |
| SEQ ID NO: 26 (Kabat) | LCDR1 | KSSQSLLDSGNQKNFLT |
| SEQ ID NO: 27 (Kabat) | LCDR2 | WASTRES |
| SEQ ID NO: 28 (Kabat) | LCDR3 | QNDYSYPYT |
| SEQ ID NO: 29 | VL | EIVLTQSPATLSLSPGERATLSCKSSQ SLLDSGNQKNFLTWYQQKPGQAPRL LIYVVASTRESGVPSRFSGSGSGTDFT FTISSLEAEDAATYYCQNDYSYPYTF GQGTKVEIK |
| SEQ ID NO: 30 | LC | EIVLTQSPATLSLSPGERATLSCKSSQ SLLDSGNQKNFLTWYQQKPGQAPRL LIYWASTRESGVPSRFSGSGSGTDFT FTISSLEAEDAATYYCQNDYSYPYTF GQGTKVEIKRTVAAPSVFIFPPSDEQL KSGTASVVCLLNNFYPREAKVQWK VDNALQSGNSQESVTEQDSKDSTYS LSSTLTLSKADYEKEIKVYACEVTHQ GLSSPVTKSFNRGEC |

TABLE 3

Amino acid sequences of the heavy and light chain leader sequences for humanized mAbs BAP049-Clone-B and BAP049-Clone-E

| | | |
|---|---|---|
| BAP049-Clone-B SEQ ID NO: 31 | HC | MAWVWTLPFLMAAAQSVQA |
| SEQ ID NO: 32 | LC | MSVLTQVLALLLLWLTGTRC |
| BAP049-Clone-E SEQ ID NO: 33 | HC | MAWVWTLPFLMAAAQSVQA |
| SEQ ID NO: 34 | LC | MSVLTQVLALLLLWLTGTRC |

TABLE 4

Constant region amino acid sequences of human IgG heavy chains and human kappa light chain HC SEQ ID NO: 35 — IgG4 (S228P) mutant constant region amino acid sequence (EU Numbering)
ASTKGPSVFP LAPCSRSTSE STAALGCLVK DYFPEPVTVS WNSGALTSGV
HTFPAVLQSS GLYSLSSVVT VPSSSLGTKT YTCNVDHKPS NTKVDKRVES
KYGPPCPPCP APEFLGGPSV FLFPPKPKDT LMISRTPEVT CVVVDVSQED
PEVQFNWYVD GVEVHNAKTK PREEQFNSTY RVVSVLTVLH
QDWLNGKEYK CKVSNKGLPS SIEKTISKAK GQPREPQVYT
LPPSQEEMTK NQVSLTCLVK GFYPSDIAVE WESNGQPENN YKTTPPVLDS
DGSFFLYSRL TVDKSRWQEG NVFSCSVMHE ALHNHYTQKS LSLSLGK LC SEQ ID NO: 36 — Human kappa constant region amino acid sequence
RTVAAPSVFI FPPSDEQLKS GTASVVCLLN NFYPREAKVQ
WKVDNALQSG NSQESVTEQD SKDSTYSLSS TLTLSKADYE
KHKVYACEVT HQGLSSPVTK
SFNRGEC HC SEQ ID NO: 37 — IgG4 (S228P) mutant constant region amino acid sequence lacing C-terminal lysine (K) (EU Numbering)
ASTKGPSVFP LAPCSRSTSE STAALGCLVK DYFPEPVTVS WNSGALTSGV
HTFPAVLQSS GLYSLSSVVT VPSSSLGTKT YTCNVDHKPS NTKVDKRVES
KYGPPCPPCP APEFLGGPSV FLFPPKPKDT LMISRTPEVT CVVVDVSQED
PEVQFNWYVD GVEVHNAKTK PREEQFNSTY RVVSVLTVLH
QDWLNGKEYK CKVSNKGLPS SIEKTISKAK GQPREPQVYT
LPPSQEEMTK NQVSLTCLVK GFYPSDIAVE WESNGQPENN YKTTPPVLDS
DGSFFLYSRL TVDKSRWQEG NVFSCSVMHE ALHNHYTQKS LSLSLG HC SEQ ID NO: 38 — IgG1 wild type
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKRVEP
KSCDKTHTCP PCPAPELLGG PSVFLFPPKP KDTLMISRTP EVTCVVVDVS
HEDPEVKFNW YVDGVEVHNA KTKPREEQYN STYRVVSVLT
VLHQDWLNGK EYKCKVSNKA LPAPIEKTIS KAKGQPREPQ VYTLPPSREE
MTKNQVSLTC LVKGFYPSDI AVEWESNGQP ENNYKTTPPV
LDSDGSFFLY SKLTVDKSRW QQGNVFSCSV MHEALHNHYT
QKSLSLSPGK HC SEQ ID NO: 39 — IgG1 (N297A) mutant constant region amino acid sequence (EU Numbering)
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKRVEP
KSCDKTHTCP PCPAPELLGG PSVFLFPPKP KDTLMISRTP EVTCVVVDVS
HEDPEVKFNW YVDGVEVHNA KTKPREEQYA STYRVVSVLT
VLHQDWLNGK EYKCKVSNKA LPAPIEKTIS KAKGQPREPQ VYTLPPSREE
MTKNQVSLTC LVKGFYPSDI AVEWESNGQP ENNYKTTPPV
LDSDGSFFLY SKLTVDKSRW
QQGNVFSCSV MHEALHNHYT QKSLSLSPGK HC SEQ ID NO: 40 — IgG1 (D265A, P329A) mutant constant region amino acid sequence (EU Numbering)
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKRVEP
KSCDKTHTCP PCPAPELLGG PSVFLFPPKP KDTLMISRTP EVTCVVVAVS
HEDPEVKFNW YVDGVEVHNA KTKPREEQYN STYRVVSVLT
VLHQDWLNGK EYKCKVSNKA LAAPIEKTIS KAKGQPREPQ
VYTLPPSREE MTKNQVSLTC LVKGFYPSDI AVEWESNGQP
ENNYKTTPPV LDSDGSFFLY SKLTVDKSRW QQGNVFSCSV
MHEALHNHYT QKSLSLSPGK TABLE 4-continued Constant region amino acid sequences of human IgG heavy chains and human kappa light chain HC SEQ ID NO: 41    IgG1 (L234A, L235A) mutant constant region amino acid sequence (EU Numbering)
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKRVEP
KSCDKTHTCP PCPAPEAAGG PSVFLFPPKP KDTLMISRTP EVTCVVVDVS
HEDPEVKFNW YVDGVEVHNA KTKPREEQYN STYRVVSVLT
VLHQDWLNGK EYKCKVSNKA LPAPIEKTIS KAKGQPREPQ VYTLPPSREE
MTKNQVSLTC LVKGFYPSDI AVEWESNGQP ENNYKTTPPV
LDSDGSFFLY SKLTVDKSRW QQGNVFSCSV MHEALHNHYT
QKSLSLSPGK Generation of Humanized BAP049-Clone-B and BAP049-Clone E and Characterization Thereof Murine anti-PD-1 monoclonal antibody BAP049 was humanized. The sequences and test samples of sixteen humanized BAP049 clones with unique variable region sequences were obtained. These clones were further analyzed for their biological functions (e.g., antigen binding and ligand blocking), structural features, and transient expression in CHO cells.

Binding Affinity and Specificity

The binding of an exemplary humanized anti-PD-1 antibody on human PD-1 protein was measured using Biacore method. The results are: $Ka=2.78\times10^5$ $M^{-1}$ $s^{-1}$; $Kd=2.13\times10^{-4}$ $s^{-1}$; $K_D=0.0827\pm0.005505$ nM.

Humanization Technology and Process

Humanization of BAP049 was performed using a combinatorial library of human germline variable region frameworks (FWs). The technology entails transferring the murine CDRs in frame to a library of human variable regions (VRs) that had been constructed by randomly combining human germ line FW1, FW2 and FW3 sequences. Only one FW4 sequence was used, which is WGQGTTVTVSS (SEQ ID NO: 45) for the heavy chain (HC) (Kabat human HC subgroup I) and FGQGTKVEIK (SEQ ID NO: 46) for the light chain (LC) (Kabat human κ subgroup I). The library of VR sequences was fused to human constant region (CR) sequences, human IgG4(S228P) of HC and human κ CR of LC, and the resulting library of whole IgG was expressed in CHO cells for screening. Screening was performed with tissue culture supernatants measuring binding avidity on antigen-expressing cells in a whole cell ELISA format or on FACS.

The humanization process was performed in a stepwise manner starting with the construction and expression of the appropriate chimeric mAb (murine VR, IgG4(S228P), human κ), which can serve as a comparator for the screening of the humanized clones. Humanization of the VR of LC and HC were performed in two independent steps. The library of humanized LC (huLC) was paired with the chimeric HC (murine VR, IgG4(S228P)) and the resulting "half-humanized" mAbs were screened for binding activity by ELISA. The huLC of clones with adequate binding activity (≥binding of chimeric mAb) were selected. Analogously, the library of humanized HC (huHC) was paired with the chimeric LC (murine VR, human κ) and screened for binding activity by ELISA. The huHC of clones with appropriate binding activity (≥binding of chimeric mAb) were selected.

The variable regions of the selected huLC and huHC were then sequenced to identify the huLC and huHC with unique sequences (some clones from the initial selection process may share the same LC or HC). The unique huLC and huHC were then randomly combined to form a small library of humanized mAbs (humAbs), which was expressed in CHO cells and screened on antigen-expressing cells in an ELISA and FACS format. Clones with binding activities that were equal or better than the binding of the chimeric comparator mAb are the final product of the humanization process.

Construction of Chimeric Antibody

Three variants of the chimeric antibody were prepared that either had a Cys, Tyr or Ser residue at position 102 of the LC sequence. The three chimeric antibodies, i.e., BAP049-chi (Cys), BAP049-chi (Tyr), and BAP049-chi (Ser) (also known as BAP049-chi, BAP049-chi-Y, and BAP049-chi-S, respectively), were expressed in CHO cells and tested for their ability to compete with labeled murine antibody for binding to PD-1 expressing Jurkat cells. The three variants were indistinguishable in the competition experiment. The results show that the three chimeric mAbs (Cys, Tyr, Ser) compete equally well with the binding of the labeled murine mAb BAP049. The slight difference between the chimeric mAb curves and the murine mAb curve is probably due to the different methods used for determining mAb concentrations. The concentration of the murine mAb was determined by OD280 measurement, whereas the chimeric mAb concentrations in supernatants were determined with an ELISA using an IgG4 standard. The germline residue Tyr was selected for humanized antibodies.

Humanized Antibody Clones

The process of humanization yielded sixteen clones with binding affinities comparable to that of the chimeric antibody. In addition to binding data, for each clone, the VR sequences were provided along with a sample of the mAb. The samples had been prepared by transient transfections of CHO cells and were concentrated tissue culture supernatants. The antibody concentrations in the solutions had been determined by an IgG4-specific ELISA.

The sixteen unique clones are combinations of four unique HC sequences and nine unique LC sequences. For the HC FW regions, the HC sequences are combinations of one of two different VHFW1, one of three different VHFW2, and one of two different VHFW3 sequences. For the LC FW regions, the LC sequences are combinations of one of five different VLFW1, one of three different VLFW2, and one of four different VLFW3 sequences. The amino acid and nucleotide sequences of the heavy and light chain variable domains for the humanized BAP049 clones B and E are shown in Table 2. The amino acid and nucleotide sequences of the heavy and light chain CDRs of the humanized BAP049 clones are also shown in Table 2.

Selection of Humanized Clones

Selected clones including clones B and E were further tested for their ability to block the binding of PD-L1 and PD-L2 to PD-1 and for enhancing T cell activity in vitro assays with human PBMC.

Expression of Humanized Anti-PD-1 Antibody, BAP049

Five humanized clones were selected for evaluation of expression in Chinese Hamster Ovary (CHO) cells.

Single gene vectors (SGVs) were constructed using Lonza's GS Xceed vectors (IgG4proΔk for heavy chain and Kappa for light chain). The SGVs were amplified and transiently co-transfected into CHOK1SV GS-KO cells for expression at a volume of 2.8 L.

Expression cultures were harvested Day 6 post-transfection and clarified by centrifugation and sterile filtration. The clarified cell culture supernatant was purified using one-step Protein A chromatography. Product quality analysis in the form of SE-HPLC, SDS-PAGE, IEF, and LAL was carried out using purified material at a concentration of 1 mg/ml including an antibody as a control sample.

Vector Construction

The sequences of the light and heavy chain variable domain encoding regions were synthesised by GeneArt AG. Light chain variable domain encoding regions were sub-cloned into pXC-Kappa and heavy chain variable domain encoding regions into pXC-IgG4pro ΔK vectors respectively using the N-terminal restriction site Hind III and the C-terminal restriction sites BsiWI (light chain) and ApaI (heavy chain). Positive clones were screened by PCR amplification (primers 1053: GCTGACAGACTAACA-GACTGTTCC (SEQ ID NO: 47) and 1072: CAAATGTGGTATGGCTGA (SEQ ID NO: 48)) and verified by restriction digest (using a double digest of EcoRI-HF and HindIII-HF) and nucleotide sequencing of the gene of interest.

DNA Amplification

A single bacterial colony was picked into 15 ml Luria Bertani (LB) medium (LB Broth, Sigma-Aldrich, L7275) containing 50 ng/ml ampicillin and incubated at 37° C. overnight with shaking at 220 rpm. The resulting starter culture was used to inoculate 1 L Luria Bertani (LB) medium containing 50 ng/ml ampicillin and incubated at 37° C. overnight with shaking at 220 rpm. Vector DNA was isolated using the QIAGEN Plasmid Plus Gigaprep system (QIAGEN, 12991). In all instances, DNA concentration was measured using a Nanodrop 1000 spectrophotometer (Thermo-Scientific) and adjusted to 1 mg/ml with EB buffer (10 mM Tris-Cl, pH 8.5). DNA quality for the single gene vectors was assessed by measuring the absorbance ratio A260/A280. This was found to be between 1.88 and 1.90.

Culture of CHOK1SV GS-KO Cells

CHOK1SV GS-KO cells were cultured in CD-CHO media (Invitrogen, 10743-029) supplemented with 6 mM glutamine (Invitrogen, 25030-123). Cells were incubated in a shaking incubator at 36.5° C., 5% $CO_2$, 85% humidity, 140 rpm. Cells were routinely sub-cultured every 3-4 days, seeding at $2 \times 10^5$ cells/ml and were propagated in order to have sufficient cells available for transfection. Cells were discarded by passage 20.

Transient Transfections of CHOK1SV GS-KO Cells

Transient transfections were performed using CHOK1SV GS-KO cells which had been in culture a minimum two weeks. Cells were sub-cultured 24 h prior to transfection and cell viability was >99% at the time of transfection.

All transfections were carried out via electroporation using a Gene Pulse MXCell (Bio-Rad), a plate based system for electroporation. For each transfection, viable cells were resuspended in pre-warmed media to $2.86 \times 10^7$ cells/ml. 80 μg DNA (1:1 ratio of heavy and light chain SGVs) and 700 μl cell suspension were aliquoted into each cuvette/well. Cells were electroporated at 300 V, 1300 μF. Transfected cells were transferred to pre-warmed media in Erlenmeyer flasks and the cuvette/wells rinsed twice with pre-warmed media which was also transferred to the flasks. Transfected cell cultures were incubated in a shaking incubator at 36.5° C., 5% $CO_2$, 85% humidity, 140 rpm for 6 days. Cell viability and viable cell concentrations were measured at the time of harvest using a Cedex HiRes automated cell counter (Roche).

Characterization of Humanized Anti-PD-1 Antibodies

Binding Affinity and Specificity

The binding of an exemplary humanized anti-PD-1 antibodies including Clone B and Clone E as shown in Table 2 on human PD-1 protein was measured using Biacore method. The results are: Ka=$2.78 \times 10^5$ $M^{-1}$ $s^{-1}$; Kd=$2.13 \times 10^{-4}$ $s^{-1}$; $K_D$=0.0827±0.005505 nM.

The binding of the same humanized anti-PD-1 antibody on human PD-1-expressing 300.19 cells was measured using FACS analysis. The result shows that the anti-PD-1 antibody (human IgG4) binds with high affinity to human PD-1 compared to a human IgG4 isotype control.

The exemplary humanized anti-PD-1 antibody was found to exhibit high affinity to cynomolgus PD-1 protein and cynomolgus PD-1-expressing 300.19 cells. As measured by Biacore method, the anti-PD-1 antibody binds to cynomolgus PD-1 with a $K_D$ of 0.093±0.015 nM. The binding affinity to cynomolgus PD-1 is comparable to its binding affinity to human PD-1.

Additional binding analyses show that the exemplary humanized anti-PD-1 antibody is not cross-reactive with mouse PD-1 or cross-reactive with parental cell line.

Blocking of Interactions Between PD-1 and its Ligands

The ability of the exemplary humanized anti-PD-1 antibody to block the interactions between PD-1 and both of its known ligands, PD-L1 and PD-L2 was examined. The results show that the anti-PD-1 antibody blocked the binding of PD-L1 and PD-L2 on human PD-1-expressing 300.19 cells compared to human IgG4 isotype control and no antibody control. The anti-PD-1 antibody blocked PD-L1 binding on the 300.19 cells with an IC50 of 0.94±0.15 nM. The same antibody blocked PD-L2 binding on the 300.19 cells with an IC50 of 1.3±0.25 nM.

Biological Activity and Function of Anti PD-1 Antibodies

In other embodiments, the aforesaid antibody molecules are capable of binding to human PD-1 with a dissociation constant ($K_D$) of less than about 0.2 nM.

In some embodiments, the aforesaid antibody molecules bind to human PD-1 with a $K_D$ of less than about 0.2 nM, 0.15 nM, 0.1 nM, 0.05 nM, or 0.02 nM, e.g., about 0.13 nM to 0.03 nM, e.g., about 0.077 nM to 0.088 nM, e.g., about 0.083 nM, e.g., as measured by a Biacore method.

In other embodiments, the aforesaid antibody molecules bind to cynomolgus PD-1 with a $K_D$ of less than about 0.2 nM, 0.15 nM, 0.1 nM, 0.05 nM, or 0.02 nM, e.g., about 0.11 nM to 0.08 nM, e.g., about 0.093 nM, e.g., as measured by a Biacore method.

In certain embodiments, the aforesaid antibody molecules bind to both human PD-1 and cynomolgus PD-1 with similar $K_D$, e.g., in the nM range, e.g., as measured by a Biacore method. In some embodiments, the aforesaid antibody molecules bind to a human PD-1-Ig fusion protein with a $K_D$ of less than about 0.1 nM, 0.075 nM, 0.05 nM, 0.025 nM, or 0.01 nM, e.g., about 0.04 nM, e.g., as measured by ELISA.

In some embodiments, the aforesaid antibody molecules bind to Jurkat cells that express human PD-1 (e.g., human PD-1-transfected Jurkat cells) with a $K_D$ of less than about 0.1 nM, 0.075 nM, 0.05 nM, 0.025 nM, or 0.01 nM, e.g., about 0.06 nM, e.g., as measured by FACS analysis.

In some embodiments, the aforesaid antibody molecules bind to cynomolgus T cells with a $K_D$ of less than about 1 nM, 0.75 nM, 0.5 nM, 0.25 nM, or 0.1 nM, e.g., about 0.4 nM, e.g., as measured by FACS analysis.

In some embodiments, the aforesaid antibody molecules bind to cells that express cynomolgus PD-1 (e.g., cells transfected with cynomolgus PD-1) with a $K_D$ of less than about 1 nM, 0.75 nM, 0.5 nM, 0.25 nM, or 0.01 nM, e.g., about 0.6 nM, e.g., as measured by FACS analysis.

In other embodiments, the aforesaid antibody molecules are capable of reducing binding of PD-1 to PD-L1, PD-L2, or both, or a cell that expresses PD-L1, PD-L2, or both. In some embodiments, the aforesaid antibody molecules reduce (e.g., block) PD-L1 binding to a cell that expresses PD-1 (e.g., human PD-1-expressing 300.19 cells) with an IC50 of less than about 1.5 nM, 1 nM, 0.8 nM, 0.6 nM, 0.4 nM, 0.2 nM, or 0.1 nM, e.g., between about 0.79 nM and about 1.09 nM, e.g., about 0.94 nM, or about 0.78 nM or less, e.g., about 0.3 nM. In some embodiments, the aforesaid antibodies reduce (e.g., block) PD-L2 binding to a cell that expresses PD-1 (e.g., human PD-1-expressing 300.19 cells) with an IC50 of less than about 2 nM, 1.5 nM, 1 nM, 0.5 nM, or 0.2 nM, e.g., between about 1.05 nM and about 1.55 nM, or about 1.3 nM or less, e.g., about 0.9 nM.

In other embodiments, the aforesaid antibody molecules are capable of enhancing an antigen-specific T cell response.

In some embodiments, the aforesaid antibody molecules increase the expression of IL-2 from cells activated by Staphylococcal enterotoxin B (SEB) (e.g., at 25 µg/mL) by at least about 2, 3, 4, 5-fold, e.g., about 2 to 3-fold, e.g., about 2 to 2.6-fold, e.g., about 2.3-fold, compared to the expression of IL-2 when an isotype control (e.g., IgG4) is used, e.g., as measured in a SEB T cell activation assay or a human whole blood ex vivo assay.

In some embodiments, the aforesaid antibody molecules increase the expression of IFN-γ from T cells stimulated by anti-CD3 (e.g., at 0.1 µg/mL) by at least about 2, 3, 4, 5-fold, e.g., about 1.2 to 3.4-fold, e.g., about 2.3-fold, compared to the expression of IFN-γ when an isotype control (e.g., IgG4) is used, e.g., as measured in an IFN-γ activity assay.

In some embodiments, the aforesaid antibody molecules increase the expression of IFN-γ from T cells activated by SEB (e.g., at 3 pg/mL) by at least about 2, 3, 4, 5-fold, e.g., about 0.5 to 4.5-fold, e.g., about 2.5-fold, compared to the expression of IFN-γ when an isotype control (e.g., IgG4) is used, e.g., as measured in an IFN-γ activity assay.

In some embodiments, the aforesaid antibody molecules increase the expression of IFN-γ from T cells activated with an CMV peptide by at least about 2, 3, 4, 5-fold, e.g., about 2 to 3.6-fold, e.g., about 2.8-fold, compared to the expression of IFN-γ when an isotype control (e.g., IgG4) is used, e.g., as measured in an IFN-γ activity assay.

In some embodiments, the aforesaid antibody molecules increase the proliferation of CD8+ T cells activated with an CMV peptide by at least about 1, 2, 3, 4, 5-fold, e.g., about 1.5-fold, compared to the proliferation of CD8+ T cells when an isotype control (e.g., IgG4) is used, e.g., as measured by the percentage of CD8+ T cells that passed through at least n (e.g., n=2 or 4) cell divisions.

In certain embodiments, the aforesaid antibody molecules has a Cmax between about 100 µg/mL and about 500 µg/mL, between about 150 µg/mL and about 450 µg/mL, between about 250 µg/mL and about 350 µg/mL, or between about 200 µg/mL and about 400 µg/mL, e.g., about 292.5 µg/mL, e.g., as measured in monkey.

In certain embodiments, the aforesaid antibody molecules has a $T_{1/2}$ between about 250 hours and about 650 hours, between about 300 hours and about 600 hours, between about 350 hours and about 550 hours, or between about 400 hours and about 500 hours, e.g., about 465.5 hours, e.g., as measured in monkey.

In some embodiments, the aforesaid antibody molecules bind to PD-1 with a Kd slower than $5\times10^{-4}$, $1\times10^{-4}$, $5\times10^{-5}$, or $1\times10^{-5}$ s$^{-1}$, e.g., about $2.13\times10^{-4}$ s$^{-1}$, e.g., as measured by a Biacore method. In some embodiments, the aforesaid antibody molecules bind to PD-1 with a Ka faster than $1\times10^{4}$, $5\times10^{4}$, $1\times10^{5}$, or $5\times10^{5}$ M$^{-1}$ s$^{-1}$, e.g., about $2.78\times10^{5}$ M$^{-1}$ s$^{-1}$, e.g., as measured by a Biacore method.

Additional Combination Partners

The combination partners of the anti-PD-1 antibody and the anti M-CSF antibody in any embodiment are preferably formulated or used to be jointly therapeutically active. This means in particular that there is at least one beneficial effect, e.g. a mutual enhancing of the effect of the combination partners, in particular, e.g., a synergism, a more than additive effect, additional advantageous effects (e.g. a further therapeutic effect not found for any of the single antibodies), less side effects, and/or combined therapeutic effect in a non-effective dosage of one or both of the combination partners. For example, the term "jointly (therapeutically) active" may mean that the compounds may be given separately or sequentially (in a chronically staggered manner, especially a sequence-specific manner) in such time intervals that they preferably, in the warm-blooded animal, especially human, to be treated, and still show a (preferably enhanced, more than additive, or synergistic) interaction (joint therapeutic effect). A joint therapeutic effect can, inter alia, be determined by reduction in tumor volume or reduction in symptoms and as described below.

In one aspect, the invention relates to treatment of a subject in vivo using the combination of an anti-PD-1 antibody molecule and an anti-M-CSF antibody molecule such that growth of cancerous tumors as described herein are inhibited or reduced. The anti-PD-1 antibody and the anti-M-CSF antibody molecule combination can be used alone to inhibit the growth of cancerous tumors or can be used in combination with one or more of: a standard of care treatment (e.g., for cancers), another antibody or antigen-binding fragment thereof, an immunomodulator (e.g., an activator of a costimulatory molecule or an inhibitor of an inhibitory molecule); or a vaccine, e.g., a therapeutic cancer vaccine other forms of cellular immunotherapy.

In one example, the combination described herein can be used for the treatment of breast cancer such as endocrine receptor (estrogen or progesterone receptor) positive, HER2 positive, triple negative (not positive to receptors for estrogen, progesterone, or HER2) or triple positive (positive for estrogen receptors, progesterone receptors and HER2). Cancer subjects receiving the combination can be patients who have been previously treated with standard of care (will depend on the stage of breast cancer) or are being treated with standard of care patients or who have not yet received any treatment. In one example, the combination described herein is used to treat patients having advanced triple negative breast cancer who have been treated or who are receiving standard of care but show disease progression.

In another example, the combination described herein can be used for the treatment of melanoma. Cancer subjects receiving the combination can be patients who have been previously treated or are being treated with standard of care (e.g., carboplatin with paclitaxel or Carboplatin/Gemcitibine, or paclitaxel) or are resistant or refractory to other immunomodulatory checkpoint inhibitors (e.g, PD-1 or PD-L1) or patients who have not yet received any treatment. In one example, the combination described herein is used to treat patients having melanoma who have been treated with PD-1 or PD-L1 and who are resistant or refractory to such treatment or who are receiving standard of care but show disease progression.

In another example, the combination described herein can be used for the treatment of ovarian cancer. Cancer subjects receiving the combination can be patients who have been previously treated or are being treated with standard of care (e.g., carboplatin with paclitaxel or Carboplatin/Gemcitibine, or paclitaxel) or patients who have not yet received any treatment. In one example, the combination described herein is used to treat patients having advanced ovarian cancer who have been treated with standard of care or are receiving standard of care but show disease progression.

In one example, the combination described herein can be used for the treatment of pancreatic cancer. Cancer subjects receiving the combination can be patients with pancreatic cancer who have been previously treated with standard of care (e.g., gemcitabine), or are being treated with standard of care, or patients who have not yet received any treatment. In one example, the combination described herein is used to treat patients having advanced pancreatic cancer who have been treated with standard of care or who are receiving the standard of care but show disease progression. The combination described herein can be administered to those who are receiving the standard of care or who have received the standard of care.

In another example, the combination described herein can be used for the treatment of glioblastoma. Cancer subjects receiving the combination can be patients who have been previously treated with standard of care, or are being treated with standard of care, or patients who have not yet received any treatment. In one example, the combination described herein is used to treat patients having glioblastoma who have been treated with standard of care but show disease progression.

In another example, the combination described herein can be used for the treatment of lung cancer such as non-small cell lung cancer (NSCLC), lung adenocarcinoma or squamous cell lung cancer. Cancer subjects receiving the combination can be patients with lung cancer who have been previously treated with standard of care (e.g., carboplatin/gemcitabine or paclitaxel) or are being treated with standard of care or patients who have not yet received any treatment. In one example, the combination described herein is used to treat patients having lung cancer who have been treated with standard of care but show disease progression.

In another example, the combination described herein can be used for the treatment of kidney renal cell carcinoma. Cancer subjects receiving the combination can be patients who have been previously treated with standard of care, or are being treated with standard of care or patients who have not yet received any treatment. In one example, the combination described herein is used to treat patients having kidney renal cell carcinoma who have been treated with standard of care but show disease progression.

In another example, the combination described herein can be used for the treatment of diffuse large b cell lymphoma. Cancer subjects receiving the combination can be patients who have been previously treated with standard of care, or are being treated with standard of care, or patients who have not yet received any treatment. In one example, the combination described herein is used to treat patients having diffuse large b cell lymphoma who have been treated with standard of care but show disease progression.

In another example, the combination described herein can be used for the treatment of mesothelioma. Cancer subjects receiving the combination can be patients who have been previously treated with standard of care, or are being treated with standard of care or patients who have not yet received any treatment. In one example, the combination described herein is used to treat patients having mesothelioma who have been treated with standard of care but show disease progression.

In another example, the combination described herein can be used for the treatment of nasopharyngeal carcinoma. Cancer subjects receiving the combination can be patients who have been previously treated or are being treated with standard of care with standard of care or patients who have not yet received any treatment. In one example, the combination described herein is used to treat patients having nasopharyngeal carcinoma who have been treated with standard of care but show disease progression.

In yet another example, the combination described herein can be used for the treatment of a cancer which is resistant or refractory to immunomodulator such as an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFR beta. In another example the immunomodulator is anti-PD-1 or anti-PD-L1. In this example, the combination described herein is used to treat patients having advanced triple negative breast cancer who have been previously treated with anti-PD-1 or anti-PDL1 but show disease progression. In another example, the combination described herein is used to treat patients having melanoma who have been previously treated with anti-PD-1 or anti-PDL1 but show disease progression.

Thus the combination of the invention provides a method of inhibiting growth of tumor cells in a subject, comprising administering to the subject a therapeutically effective amount of the combination described herein. In another embodiment, the combination of the invention can be administered alone or in combination with one or more other agents, and the combination can be administered in either order or simultaneously. In one example, the combination therapy disclosed herein can include a composition of the present invention co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the combination described herein can be administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

By "in combination with," it is not intended to imply that therapy or therapeutic agents must be administered at the same time and/or formulated for delivery together, although these methods of delivery are within the scope described herein. The anti-PD-1 antibody and anti-M-CSF molecules can be administered concurrently with, prior to, or subsequent to, one or more other additional therapies or therapeutic agents. The anti-PD-1 antibody and anti-M-CSF molecules and the other agent or therapeutic protocol can be administered in any order. In general, each agent will be administered at a dose and/or on a time schedule determined for that agent. In will further be appreciated that the additional therapeutic agent utilized may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

In certain embodiments, the combination of the invention are administered in combination with one or more other inhibitors of PD-1, PD-L1 and/or PD-L2 known in the art. The antagonist may be an antibody, an antigen binding fragment thereof, an immunoadhesin, a fusion protein, or oligopeptide. In some embodiments, the other anti-PD-1 antibody is chosen from MDX-1106, Merck 3475 or CT-011. In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224. In some embodiments, the PD-L1 inhibitor is anti-PD-L1 antibody. In some embodiments, the anti-PD-L1 binding antagonist is chosen from YW243.55.S70, MPDL3280A, MEDI-4736, MSB-0010718C, or MDX-1105. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634.

MDX-1106, also known as MDX-1106-04, ONO-4538 or BMS-936558, is an anti-PD-1 antibody described in WO2006/121168. Merck 3745, also known as MK-3475 or SCH-900475, is an anti-PD-1 antibody described in WO2009/114335. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. In other embodiments, the anti-PD-1 antibody is pembrolizumab. Pembrolizumab (Trade name Keytruda formerly lambrolizumab also known as MK-3475) disclosed, e.g., in Hamid, O. et al. (2013) *New England Journal of Medicine* 369 (2): 134-44. AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

Exemplary other agents that can be combined with the combination of the invention can include standard of care chemotherapeutic agent including, but not limited to, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), vinorelbine (Navelbine®), Ibrutinib, idelalisib, and brentuximab vedotin.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil Nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids that can be used in combination with the anti-PD-1 antibody molecules, alone or in combination with another immunomodulator (e.g., an anti-LAG-3, anti-PD-L1 or anti-TIM-3 antibody molecule), include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Compositions and Uses

The present invention relates to a pharmaceutical product or a commercial package comprising a combination product according to the invention described herein, in particular together with instructions for simultaneous, separate or sequential use (especially for being jointly active) thereof in the treatment of cancer. In one aspect, the present invention provides compositions, e.g., pharmaceutically acceptable compositions, which include a PD-1 antibody molecule as described herein and an M-CSF antibody molecule as described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g. by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the combination disclosed herein is administered by intravenous infusion or injection. In another preferred embodiment, the combination disclosed herein is administered by intramuscular or subcutaneous injection.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Pharmaceutical compositions for use in the disclosed methods may be manufactured in conventional manner. The use of antibodies as the active ingredient of pharmaceuticals is now widespread, including the products Herceptin® (trastuzumab), Rituxan® (rituximab), Synagis® (palivizumab), etc. Techniques for lyophilisation, preparation of aqueous formulations, and purification of antibodies to a pharmaceutical grade are well known in the art.

Antibodies are typically formulated either in aqueous form ready for parenteral administration or as lyophilisates for reconstitution with a suitable diluent prior to administration. In some embodiments of the disclosed methods and uses, the antibodies of the present invention are formulated as a lyophilisate. Suitable lyophilisate formulations can be reconstituted in a small liquid volume (e.g., 2 ml or less) to allow subcutaneous administration and can provide solutions with low levels of antibody aggregation. For immediate administration it is dissolved in a suitable aqueous carrier, for example sterile water for injection or sterile buffered physiological saline. If it is considered desirable to make up a solution of larger volume for administration by infusion rather than a bolus injection, may be advantageous to incorporate human serum albumin or the patient's own heparinised blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution.

Administration Methods and Rates

The antibody molecules of the combination disclosed herein can be administered by a variety of methods known in the art, although for many therapeutic applications, the preferred route/mode of administration is intravenous injection or infusion. See for example, Sachs et al., Optimal Dosing for Targeted Therapies in Oncology: Drug Development Cases Leading by Example, Clin. Cancer Res; 22(6) 2016; Bai et al, A Guide to Rational Dosing of Monoclonal Antibodies, Clin. Pharmacokinet. 2012: 51 (2) 119-135; Le Tourneau, J., Dose Escalation Methods in Phase I Cancer Clinical Trials, J Natl Cancer Inst 2009; 101:708-720; Wang, D. et al., Fixed Dosing Versus Body Size-Based Dosing of Monoclonal Antibodies in Adult Clinical Trials, J Clin Pharmacol 2009; 29:1012-1024; Hempel, G. et ano, Flat-Fixed Dosing Versus Body Surface Aread-Based Dosing of Anticancer Drugs: There Is a Difference, The Oncologist 2007: 12:924-926, Mathijssen, R., Flat-Fixed Dosing Versus Body Surface Area-Based Dosing of Anticancer Drugs in Adults: Does It Make a Difference?, The Oncologist, 2007; 12:913-923; Leveque, Evaluation of Fixed Dosing of New Anticancer Agents in Phase I Studies, Anticancer Research 28:300275-2078 (2008), Gurney, How to calculate the dose of chemotherapy, British Journal of Cancer (2002) 86, 1297-1302; For example, the antibody molecules can be administered by intravenous infusion at a rate of more than 20 mg/min, e.g., 20-40 mg/min, and typically greater than or equal to 40 mg/min to reach a dose of about 35 to 440 $mg/m^2$, typically about 70 to 310 $mg/m^2$, and more typically, about 110 to 130 $mg/m^2$. In embodiments, the antibody molecules can be administered by intravenous infusion at a rate of less than 10 mg/min; preferably less than or equal to 5 mg/min to reach a dose of about 1 to 100 $mg/m^2$, preferably about 5 to 50 $mg/m^2$, about 7 to 25 $mg/m^2$ and more preferably, about 10 $mg/m^2$ The route and/or mode of administration will vary depending upon the desired results.

Dosage Regimens

Dosage regimens are adjusted to provide the optimum desired response (e.g., a therapeutic response). For example, a single bolus may be administered, several divided doses may be administered over time or the dose may be proportionally reduced or increased as indicated by the exigencies of therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Weight Dosage

An antibody can be dosed according to the weight of the patient. An exemplary, non-limiting range for a therapeutically or prophylactically effective amount of an antibody molecule is 0.1-30 mg/kg, more preferably 1-25 mg/kg. Dosages and therapeutic regimens of the combination disclosed herein can be determined by a skilled artisan. They can be delivered separately or simultaneously. In certain embodiments, the anti-PD-1 antibody is administered by injection (e.g., subcutaneously or intravenously) at a dose of about 1 to 40 mg/kg, e.g., 1 to 30 mg/kg, e.g., about 3 to 25 mg/kg, about 3 to 20 mg/kg, about 1 to 5 mg/kg, 1 to 10 mg/kg, 3 to 10 mg/kg, 5 to 15 mg/kg, 10 to 20 mg/kg, 15 to 25 mg/kg, or about 3 mg/kg and the anti-M-CSF antibody is administered by injection (e.g., subcutaneously or intravenously) at a dose of about 1 to 40 mg/kg, e.g., 1 to 30 mg/kg, e.g., about 3 to 25 mg/kg, about 10 to 20 mg/kg, about 1 to 5 mg/kg, 3 to 10 mg/kg, 1 to 10 mg/kg, 5 to 15 mg/kg, 10 to 20 mg/kg, 15 to 25 mg/kg, or about 3 mg/kg.

Flat Dosage

Antibodies can also be administered to patients as a flat dosage, that is giving a fixed or predetermined amount of dosage to each patient. The terms flat dosage and fixed dosage are used interchangeably. Flat or fixed dosing can be beneficial to patients, for example, to save drug supply and to reduce pharmacy errors.

In some embodiments, the anti-PD-1 antibody molecule is administered by injection (e.g., subcutaneously or intravenously) at a dose (e.g., a flat dose) of about 200 mg to 500 mg, e.g., about 250 mg to 450 mg, about 300 mg to 400 mg, about 250 mg to 350 mg, about 350 mg to 450 mg, or about 300 mg or about 400 mg. The dosing schedule (e.g., flat dosing schedule) can vary from e.g., once a week to once every 2, 3, 4, 5, or 6 weeks. In one embodiment, the anti-PD-1 antibody molecule is administered at a dose from about 300 mg to 400 mg once every three weeks or once every four weeks. In one embodiment, the anti-PD-1 antibody molecule is administered at a dose from about 300 mg once every three weeks. In one embodiment, the the anti-PD-1 antibody molecule is administered at a dose from about 400 mg once every four weeks. In one embodiment, the anti-PD-1 antibody molecule is administered at a dose from about 300 mg once every four weeks. In one embodiment, the anti-PD-1 antibody molecule is administered at a dose from about 400 mg once every three weeks.

The anti-M-CSF antibody can likewise be administered as a flat dosage. In some embodiments, the anti-M-CSF antibody molecule is administered by injection (e.g., subcutaneously or intravenously) at a dose (e.g., a flat dose) of about 200 mg to 500 mg, e.g., about 250 mg to 450 mg, about 300 mg to 400 mg, about 250 mg to 350 mg, about 350 mg to 450 mg, or about 300 mg or about 400 mg. Additionally, the ant-M-CSF antibody molecule can also be administered by injection at a flat dose of about 300 mg to 800 mg, including about 800 mg. The dosing schedule (e.g., flat dosing schedule) can vary from e.g., once a week to once every 2, 3, 4, 5, or 6 weeks. In one embodiment, the anti-M-CSF antibody molecule is administered at a dose from about 300 mg to 400 mg once every three weeks or once every four weeks. In one embodiment, the anti-M-CSF antibody molecule is administered at a dose from about 300 mg once every three weeks. In one embodiment, the anti-M-CSF antibody molecule is administered at a dose from about 400 mg once every four weeks. In one embodiment, the anti-M-CSF antibody molecule is administered at a dose from about 300 mg once every four weeks. In one embodiment, the anti-M-CSF antibody molecule is administered at a dose from about 400 mg once every three weeks.

Dosing Schedule

The dosing schedule can vary from e.g., once a week to once every 2, 3, or 4 weeks. In one embodiment, the anti-PD-1 antibody and the anti-M-CSF antibody or both molecules are administered at a dose from about 3 to 10 mg/kg every other week. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Exemplary doses for the three (or more) agent regimens are as follows. The anti-PD-1 antibody and the anti-M-CSF antibody or both molecules can be administered, e.g., at a dose of about 1 to 40 mg/kg, e.g., 1 to 30 mg/kg, e.g., about 5 to 25 mg/kg, about 10 to 20 mg/kg, about 1 to 5 mg/kg, or about 3 mg/kg. The M-CSF antibody molecule can be administered, e.g., at a dose of about 1 to 40 mg/kg, e.g., 1 to 30 mg/kg, e.g., about 5 to 25 mg/kg, about 10 to 20 mg/kg, about 1 to 5 mg/kg, or about 3 mg/kg.

Biomarkers

The invention further includes selecting patients that may benefit most from treatment with the combination on an anti-PD-1 antibody molecule and an anti-M-CSF antibody molecule. Selection of patients can be achieved by determining for the presence of PD-1 or the presence of tumor associated macrophages (TAMS). While not wishing to be bound by theory, in some embodiments, a patient is more likely to respond to treatment with the combination of the invention if the patient has a cancer that highly expresses PD-L1, and/or the cancer is infiltrated by anti-tumor immune cells, e.g., TILs and/or has a high TAMS level, e.g., determined by looking for CD163 or CD163/CD8 as described below.

In addition other potential predictors of potential efficacy of the combination include FoxP3, PD-L1 and CD68 expression levels at baseline (modulation of TAM and TIL phenotype) and anti-tumor activity endpoints (eg., over all response rate). In one embodiment of the present invention a patient's blood could be assayed for either CD163 or CD163/CD8 as a single predictor for the efficacy of the combination.

The pharmacodynamics effect of the combination can potentially be assessed by CD8, CD163, FoxP3, PD-L1, CD68 expression levels at baseline and post-baseline (modulation of TAM and TIL phenotype), CD4, LAG3, or TIM3, (as well as CD80, LKB2, CCL2 if available). In addition, systemic cytokine levels at baseline and post-baseline can be measured to assess pharmacodynamics (e.g., GM-CSF, IFN-γ, IL-10, IL-18, IL-2, IL-3, IL-4, IL-5, IL-6, IL-7, IL-8, MCP-1, MIP-1 α MIP-1 β, TNF-α, or TNF-β).

ORR per RECIST v1.1 in BRCA1/BRCA2 mutant and non-mutant TNBC patients, respectively can be used to evaluate whether BRCA1 and BRCA2 status influence response to treatment in TNBC patients. ORR per RECIST v1.1 according to MSI status and mutational burden evaluate whether microsatellite instability status and mutational burden influence the overall response rate. The anti-tumor activity of the combination of MCS110 with PDR001 in melanoma patients with intrinsic or acquired resistance to PD-1/PDL-1 targeted therapies, can be evaluated ORR per RECIST v1.1 in melanoma patients with intrinsic or acquired resistance to PD-1 (per clinical history), respectively.

Selection of Patients Having PD-1

In one example, determining for the presence of PD-1 can be to determine the anti-tumor immune cells by assaying for cells positive for CD8, PD-L1, and/or IFN-γ; thus levels of CD8, PD-L1, and/or IFN-γ can serve as a readout for levels of TILs in the microenvironment. In certain embodiments, the cancer microenvironment is referred to as triple-positive for PD-L1/CD8/IFN-γ.

Accordingly, in certain aspects, this application provides methods of determining whether a tumor sample is positive for one or more of PD-L1, CD8, and IFN-γ, and if the tumor sample is positive for one or more, e.g., two, or all three, of the markers, then administering to the patient a therapeutically effective amount of an anti-PD-1 antibody molecule, optionally in combination with one or more other immunomodulators or anti-cancer agents.

In the following indications, a large fraction of patients are triple-positive for PD-L1/CD8/IFN-γ: TN breast cancer. Regardless of whether a large or small fraction of patients is triple-positive for these markers, screening the patients for these markers allows one to identify a fraction of patients that has an especially high likelihood of responding favorably to therapy with a PD-1 antibody (e.g., a blocking PD-1 antibody) in combination with M-CSF-1 and optionally one or more other immunomodulators (e.g., an anti-TIM-3 antibody molecule, an anti-LAG-3 antibody molecule, or an anti-PD-L1 antibody molecule) and/or anti-cancer agents.

In some embodiments, the cancer sample is classified as triple-positive for PD-L1/CD8/IFN-γ. This measurement can roughly be broken down into two thresholds: whether an individual cell is classified as positive, and whether the sample as a whole is classified as positive. First, one can measure, within an individual cell, the level of PD-L1, CD8, and/or IFN-γ. In some embodiments, a cell that is positive for one or more of these markers is a cell that has a higher level of the marker compared to a control cell or a reference value. For example, in some embodiments, a high level of PD-L1 in a given cell is a level higher than the level of PD-L1 in a corresponding non-cancerous tissue in the patient. As another example, in some embodiments, a high level of CD8 or IFN-γ in a given cell is a level of that protein typically seen in a TIL. Second, one can also measure the percentage of cells in the sample that are positive for PD-L1, CD8, and/or IFN-γ. (It is not necessary for a single cell to express all three markers.) In some embodiments, a triple positive sample is one that has a high percentage of cells, e.g., higher than a reference value or higher than a control sample, that are positive for these markers.

In other embodiments, one can measure the levels of PD-L1, CD8, and/or IFN-γ overall in the sample. In this case, a high level of CD8 or IFN-γ in the sample can be the level of that protein typically seen in a tumor infiltrated with TIL. Similarly, a high level of PD-L1 can be the level of that protein typically seen in a tumor sample, e.g., a tumor microenvironment.

The identification of subsets of patients that are triple-positive for PD-L1/CD8/IFN-γ reveals certain sub-populations of patients that are likely to be responsive to PD-1 antibody therapy. For instance, many IM-TN (immunomodulatory, triple negative) breast cancer patients are triple-positive for PD-L1/CD8/IFN-γ. IM-TN breast cancer is described in, e.g., Brian D. Lehmann et al., "Identification of human triple-negative breast cancer subtypes and preclinical models for selection of targeted therapies", *J Clin Invest*. Jul. 1, 2011; 121(7): 2750-2767. Triple-negative breast cancers are those that do not express estrogen receptor (ER), progesterone receptor (PR) and Her2/neu. These cancers are difficult to treat because they are typically not responsive to agents that target ER, PR, and Her2/neu. Triple-negative breast cancers can be further subdivided into different classes, one of which is immunomodulatory. As described in Lehmann et al., IM-TN breast cancer is enriched for factors involved in immune cell processes, for example, one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing. Accordingly, in some embodiments, the cancer treated is a cancer that is, or is determined to be, positive for one or more marker of IM-TN breast cancer, e.g., a factor that promotes one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing.

Selection of Patients Using TAMS

The present invention is directed to the use of a combination of the anti-M-CSF antibody described in Table 1 and a PD-1 antibody described in Table 2, for the treatment of cancer such as triple negative breast cancer. Currently, there are no targeted therapies for this breast cancer subtype and the only treatment option is chemotherapy. The present invention provides for personalized therapy that maximizes the benefit and minimizes the risk of use of anti-M-CSF antibody molecule in cancer populations by identifying those patients likely to respond favorably prior to treatment with an M-CSF treatment. In one example, the present invention includes identifying patients who have cancer, such as triple negative breast cancer patient, that have a level of tumor associated macrophages (TAMs) indicative that the patient is likely to respond to treatment with an M-CSF antagonist. Specifically, the patient's level of TAMs is measured by determining the level of CD163 (e.g., mRNA or protein) in a sample from the patient and the patient's level of CD163 in turn is used to indicate whether that patient is more likely to respond favorably to M-CSF treatment. In one example, if the patient has an increased level of CD163 compared to a control than the patient is identified as a patient more likely to respond to an M-CSF antagonist. In another example, if the patient has a CD163 level equal or greater than a predetermined CD163 level ("cutoff") then the patient is identified to be a patient more likely to respond to an M-CSF antagonist. The level of CD163 expression assayed in a sample obtained from a cancer patient can be, e.g., mRNA expression and/or protein.

Preparation of Samples

Any appropriate sample or test sample of cells taken from an individual having cancer can be used. Generally, the test sample of cells or tissue sample will be obtained from the subject with cancer by biopsy or surgical resection. A sample of cells, tissue, or fluid may be removed by needle aspiration biopsy. For this, a fine needle attached to a syringe is inserted through the skin and into the tissue of interest. The needle is typically guided to the region of interest using ultrasound or computed tomography (CT) imaging. Once the needle is inserted into the tissue, a vacuum is created with the syringe such that cells or fluid may be sucked through the needle and collected in the syringe. A sample of cells or tissue may also be removed by incisional or core biopsy. For this, a cone, a cylinder, or a tiny bit of tissue is removed from the region of interest. CT imaging, ultrasound, or an endoscope is generally used to guide this type of biopsy. More particularly, the entire cancerous lesion may be removed by excisional biopsy or surgical resection. In the present invention, the test sample is typically a sample of cells removed as part of surgical resection.

The test sample of, for example tissue, may also be stored in, e.g., RNAlater (Ambion; Austin Tex.) or flash frozen and stored at −80° C. for later use. The biopsied tissue sample may also be fixed with a fixative, such as formaldehyde, paraformaldehyde, or acetic acid/ethanol. The fixed tissue sample may be embedded in wax (paraffin) or a plastic resin. The embedded tissue sample (or frozen tissue sample) may be cut into thin sections. RNA or protein may also be extracted from a fixed or wax-embedded tissue sample or a frozen tissue sample. Once a sample of cells or sample of tissue is removed from the subject with cancer, it may be processed for the isolation of RNA or protein using techniques well known in the art and as described below.

An example of extraction of RNA from a biopsy taken from a patient with cancers can include, for example, guanidium thiocyanate lysis followed by CsCl centrifugation. RNA from single cells may be obtained as described in methods for preparing cDNA libraries from single cells. In one embodiment, the RNA population may be enriched for CD163. Enrichment may be accomplished, for example, by random hexamers and primer-specific cDNA synthesis, or multiple rounds of linear amplification based on cDNA synthesis and template-directed in vitro transcription, The subject with a tumor or cancer will generally be a mammalian subject such as a primate. In an exemplary embodiment, the subject is a human.

The Presence of TAMs can be Assessed by Detecting for the Presence of CD163+

The methods disclosed herein employ, inter alia, determining the level of CD163. The level of CD163 is predictive as to whether that individual is more likely to respond to an M-CSF antagonist. In one example the level of CD163 that is predictive refers to an expression level that is higher than the median level (control) for CD163 expression in cancer or greater than a predetermined cut-off value.

In one embodiment, the level of CD163 protein expression is compared against a control, or cut off, for selecting patients for treatment with the M-CSF antagonist, e.g., the level of CD163 expression compared to a control can be predictive that the patient is likely or not likely to respond to M-CSF antagonist such as H-RX1. In one embodiment, patients having a level of expression of CD163 protein expression (also referred to as "TAMs density") above a threshold level of 10%, 15%, 20%, 30%, 40% or higher are selected for treatment with an M-CSF antagonist. The control level of CD163 can be determined essentially contemporaneously with measuring CD163 expression or may have been determined previously.

Detecting CD163 Nucleic Acid Expression

The biological sample from the patient may be assayed for the presence of CD163 expression such as mRNA by any applicable means. Increased levels of CD163 expression may be useful to predict improved response to M-CSF antagonism for patients with cancer, e.g., TBNC.

Detecting CD163 Protein

In some cases, the presence of CD163 can be determined by analyzing CD163 polypeptide products. Detection of polypeptide products can be performed using any known method in the art including, but not limited, to immunocytochemical staining, ELISA, flow cytometry, Western blot, spectrophotometry, HPLC, and mass spectrometry.

Control

As used herein, the controls for comparison can be determined by one skilled in the art. In one example, the controls are determined by choosing control samples with TAM density values that define a cut-off value. For example, the value can be a value that differentiates between e.g., test samples where the individual has a CD163 (or TAM density) of less than 15%, or test samples where the individual has a CD163 (or TAM density) of equal or greater than 15% CD163 (or TAM density); or between those test samples where the individual is likely to benefit from M-CSF antagonist therapy and those that likely would not.

In another example, the control can be a sample from a healthy volunteer or a sample from a cancer patient that is known to have a low CD163 expression (mRNA or protein), and a patient is selected for treatment when the CD163 value determined is greater than those controls.

In yet another example, the control value can be a value predetermined according to historical controls as a basis of a mathematical model. The model, also called a classifier, can be built by using the expression levels (e.g., mRNA or protein) from a collection of cancer patients (e.g., TBNCs). The mathematical model, can be, for example, any class prediction method or its variations and the derived control value can be used as the threshold. If the level of expression is at or above the threshold, the patient is more likely to respond to treatment with an M-CSF antagonist. In one embodiment, an individual is selected who has a level of CD163 expression equal or greater than the threshold, e.g., can be 15%, 20%, 30%, 40% or higher.

Selection and Treatment of Patients with Cancer

The level of CD163 nucleic acid expression or CD163 protein allows clinicians to provide a personalized therapy for cancer patients such as TBNCs, pancreatic cancer, ovarian cancer, melanoma, nasopharyngeal carcinoma, diffuse large b cell lymphoma, mesothelioma, kidney renal cell carcinoma, or glioblastoma, i.e., they allow determination of whether to selectively treat the patient with an M-CSF antagonist. In this way, a clinician can maximize the benefit and minimize the risk of M-CSF antagonism in the entire population of patients afflicted with cancer. Various aspects of the invention are described in further detail below. Additional definitions are set out throughout the specification.

Example 1

A Phase Ib clinical trial is performed with MCS110 and PDR001 administered once every 3 weeks via i.v. infusions over 30 minutes and 1 hour, respectively. The drugs will be administered separately with at least a 30 min break between the two antibodies. Infusions of each antibody can be extended to up to 2 hours if clinically indicated. The below dosing regimen is used in below Table 10.

TABLE 5

Example dosing regimen

| Study treatments | Pharmaceutical form and route of administration | Dose | Frequency and/or Regimen |
|---|---|---|---|
| MCS110 | Liquid concentrate in vial i.v. infusion | 3 mg/kg (starting dose) | Every 3 weeks |
| PDR001 | Lyophilisate in vial i.v. infusion | 100 mg (starting dose) | Every 3 weeks |

Both study drugs may be infused using the same i.v. access site. The same administration sequence is followed for all patients, i.e. PDR001 should be infused first. If an infusion reaction occurs after administration of PDR001, the subsequent MCS110 infusion is delayed until it is safe for the patient to receive MCS110 based on the clinical discretion of the investigator. The delay between PDR001 and MCS110 infusions can be up to 4 hours if clinically indicated.

A scheduled dose of ongoing study drugs may be delayed by up to 7 days to recover from previous AEs or a missed visit. If a scheduled dose of ongoing study drugs is delayed longer than 7 days due to an unresolved AE, the administration should be skipped and treatment resumed at a lower dose level (if meeting criteria for DLT) at the next scheduled dose. The assessment schedule will be shifted accordingly. Dose delays refer to all ongoing study drugs: for combination treatment both MCS110 and PDR001 and for single agent treatment MCS110 or PDR001. The dose for MCS110 study drug is calculated from the individual subjects' body weight as measured at the screening visit and subsequent visits prior to the administration.

Starting Dose

The starting dose and regimen of MCS110 will be 3 mg/kg iv every 3 weeks, corresponding to approximately 40% of the single agent dose administered in PVNS patients (10 mg/kg every 4 weeks in study NCT01643850, CMCS110X2201)) and 30% of the dose administered in combination with carboplatin/gemcitabine in TNBC (10 mg/kg every 3 weeks in study NCT02435680, CMCSZ2201).

An MCS110 dose of 10 mg/kg was well tolerated in PVNS patients and showed significant tumor reduction in PVNS patients. After a single dose of 3 mg/kg of MCS110 in healthy volunteers, it was observed that CSF-1 has been saturated by MCS110 for approximately 21 days CMCSX2101. Pharmacodynamic analyses performed in HV studies indicate that circulating biomarker response should be close to maximal with dose at or above 5 mg/kg and minimal with doses below 3 mg/kg. Considering the risk of potential overlapping toxicities, the dose of 3 mg/kg MCS110 is selected as the starting dose for the dose escalation part of the study.

The starting dose and regimen of PDR001 is 100 mg iv every 3 weeks. PDR001 has been tested up to the dose of 10 mg/kg every 2 weeks in the ongoing NCT02404441, CPRD001X2101 study. No MTD has been determined and the planned recommend phase two dose (RP2D) is 300 mg (3.75 mg/kg) given every 3 weeks or 400 mg (5 mg/kg) given every 4 weeks. Both of the proposed RP2Ds may achieve the steady mean $C_{trough}$ (C through) concentrations that are approximately 77 fold higher than the in vitro/ex vivo potency EC50 for PDR001 assessed as 0.42 µg/mL. The PDR001 exposure at a starting dose of 100 mg Q3W is within the range of those observed in the CPDR001X2101 study with no DLTs. PDR001 is expected to demonstrate antitumor activity at doses of 100 mg or above every 3 weeks.

TABLE 6

| Dose level* | Proposed dose MCS110 | Proposed dose PDR001 |
|---|---|---|
| −2** | 0.3 mg/kg Q3W | 100 mg Q3W |
| −1** | 1 mg/kg Q3W | 100 mg Q3W |
| 1 (starting dose) | 3 mg/kg Q3W | 100 mg Q3W |
| 2 | 3 mg/kg Q3W | 300 mg Q3W |
| 3 | 5 mg/kg Q3W | 300 mg Q3W |
| 4 | 10 mg/kg Q3W | 300 mg Q3W |

*It is possible for additional and/or intermediate dose levels to be added during the course of the study. Cohorts may be added at any dose level below the MTD in order to better understand safety, PK or PD
**Dose level −1 or −2 represent provisional dose levels and/or treatment doses for patients requiring a dose reduction from the starting dose level. No dose reduction below dose level −2 is permitted for this study Potential Toxicity This is the first study evaluating the combination of MCS110 and PDR001. Potential overlapping toxicities include liver enzyme elevations caused by immune induction (PDR001) or reduced elimination of liver enzymes (MCS110), higher frequency or aggravation of immune mediated adverse events and skin toxicity.

A dose-limiting toxicity (DLT) is defined as an adverse event or abnormal laboratory value of CTCAE Grade≥3 assessed as unrelated to disease, disease progression, intercurrent illness, or concomitant medications that occurs within the first two cycles of treatment with the combination treatment and meets any of the criteria included in Table XX.

Emerging data from the new field of immune-immune combination studies suggest that some immune-related adverse events have a prolonged latency. As such, the DLT window for the combination cohort in this trial is extended to the length of two cycles or 42 days.

National Cancer Institute Common Terminology Criteria for Adverse events (NCI CTCAE) version 4.03 will be used for all grading. For the purpose of dose-escalation decisions, DLTs will be considered and included in the Bayesian logistic regression model (BLRM).

For patients who do not tolerate the protocol-specified dosing schedule, dose adjustments are permitted in order to allow the patient to continue the study treatment, except during the first two cycles when dose modifications are only allowed if the patient experiences a DLT. The following guidelines need to be applied:

If a patient experiences an AE meeting the criteria for DLT as outlined in Section 6.2.4, treatment should be withheld. Dose modifications for toxicities related to the study medication are summarized in Table 6-44. Following resolution of the toxicity to Grade 1 or to the patient's baseline value, the patient may resume study treatment at a lower dose level than is being tested at that time (on the same dosing schedule), if there is no evidence of disease progression as per irRC. A decision to resume treatment following the occurrence of a DLT is at the discretion of the Investigator. Following an AE meeting criteria for DLT, if a patient resumes study treatment, it should be at the next lower dose level. Dose reductions to doses below MCS110 0.3 mg/kg/ PDR001 100 mg Q3W are not permitted. If more than 2 consecutive doses have to be skipped due to study treatment-related toxicities, then the patient must be discontinued from the study unless the patient experiences clinical benefit in the opinion of the investigator. In this case, treatment can be continued at a dose agreed by Novartis and the investigator.

If one of the study drugs is discontinued the patient may continue with the remaining study drug, if the investigator considers it to be in the patient's best interest. The dose of the remaining study drug must be agreed by Novartis and the investigator.

For diarrhea/colitis, renal, pulmonary, endocrinopathies, hepatic and skin AEs, first rule out non-inflammatory causes. If felt to be an inflammatory cause, treat according to Appendix 14.3: Recommended management algorithms for suspected toxicities, which incorporates corticosteroid therapy.

Criteria for Dose-Limiting Toxicities

TABLE 7

| For the purpose of dose escalation and cohort expansion, DLT will be defined as follows: |
|---|
| Any Grade 4 AEs will be considered DLTs with the exception of: |
| Neutropenia lasting ≤5 days that is not associated with fever or other clinical symptoms. |
| Lymphopenia or leukopenia at any grade |
| Any Grade 3 AEs will be considered DLTs with the exception of: |
| Electrolyte abnormalities that are not associated with clinical sequelae and are corrected to ≤Gr1 with appropriate management or supplementation within 72 hours of onset. |
| Infusion reaction that resolves to ≤Grade 1 within 6 hours. |
| Nausea and vomiting persisting for <2 days with optimal anti-emetic therapy. |
| Thrombocytopenia without significant bleeding. |
| Diarrhea persisting for <2 days with optimal anti-diarrhea therapy. |
| Hypertension persisting <7 days with optimal therapy. |
| Infection or fever in the absence of neutropenia persisting <7 days. |
| Rash or photosensitivity persisting <7 days after treatment. |
| Fatigue lasting <7 days. |
| Immune-related adverse events persisting at Grade3 <7 days after treatment with corticosteroids. |
| *CK elevation without associated muscle damage per investigator discretion |
| *Isolated AST elevations (without bilirubin or ALT elvations ≥Grade 1) |
| The following Grade 2 AEs will be considered as DLTs: |
| Total bilirubin with ≥CTCAE Grade 2 AST/ALT. |
| Pneumonitis persisting >7 days despite treatment with corticosteroids. |
| Eye pain or reduction of visual acuity that does not respond to topical therapy and does not improve to Grade 1 severity within 2 weeks of the initiation of topical therapy OR requires systemic treatment. |
| Other clinically significant toxicities, including a single event or multiple occurrences of the same event may be considered as DLT's. |

*MCS110 treatment results in CK and AST elevations without any association to muscle damage Radi, 2011 Am J Pathol. 2011 July; 179(1):240-7. The CK/AST elevations are caused by reduced clearance rate from the circulation due to the diminished numbers of macrophages (Kupffer cells) in the liver (Section 1.2.2.1).

TABLE 8

Dosage modifications for drug related toxicities

| Toxicity | Dose Adjustment Rules* |
|---|---|
| Hematology | |
| Grade 3 febrile neutropenia or Grade 4 neutropenia >5 days | Delay treatment until ANC ≥1000/mm$^3$ and no fever. |
| Grade 3 thrombocytopenia (TCP) with clinically significant bleeding or G4 TCP | Delay treatment for TCP with clinically significant bleeding until platelets ≥75 × 10$^9$/L and bleeding has resolved. |
| Grade 4 febrile neutropenia Grade 4 TCP >5 days | Discontinue from treatment. |
| Gastrointestinal (colitis) | |
| Grade 2 | Delay treatment until Grade ≤1 or baseline. |
| Grade 3 or 4 | Discontinue from treatment. |
| Pulmonary (pneumonitis) | |
| Grade 1 | Treatment may continue with close clinical follow up |
| Grade 2 | Delay treatment until resolved to Grade ≤1. If not resolved within 2 weeks discontinue treatment. |
| Grade 3 or 4 | Discontinue from treatment. |
| Hepatic (AST/ALT or bilirubin) | |
| Grade 2 ALT or bilirubin | Delay treatment until resolved to Grade ≤1. |
| Grade 3 ALT or bilirubin | If ALT ≤8 × ULN or Bilirubin ≤5 × ULN: delay treatment. Re-start when resolved to Grade ≤1. Decrease MCS110 1 dose level. If ALT >8 × ULN or Bilirubin >5 × ULN: discontinue from treatment. |
| Grade 4 AST/ALT or bilirubin or Grade 2 bilirubin with Grade 2 AST or ALT | Discontinue from treatment. |
| CK elevation | |
| Grade 3-4 | Monitor CK-MB isoenzyme, troponin (I or T), and creatinine. If CK-MB and troponin (I or T) are normal, creatinine ≤1.5 × baseline and patient asymptomatic, continue treatment. If CK-MB and troponin (I or T) are abnormal or creatinine (>1.5 × baseline and >ULN) or patient symptomatic, delay treatment |

TABLE 8-continued

Dosage modifications for drug related toxicities

| Toxicity | Dose Adjustment Rules* |
|---|---|
| | and explore alternative causes for elevated CK (for example myositis and rhabdomyolysis) according to local guidelines. After recovery of CK-MB, troponin (I or T) and creatinine to Grade 1 or baseline, restart treatment. Decrease MCS110 1 dose level. |
| | Renal (creatinine) |
| Grade 2 or 3 | Delay treatment until resolved to Grade ≤1 or baseline. |
| Grade 4 | Discontinue from treatment. |
| | Endocrine |
| Grade 2 or 3 | Delay treatment until ≤Grade 1. |
| Grade 4 | Discontinue from treatment or discuss restart with Novartis following adequate replacement treatment. |
| | Ocular (uveitis) |
| Grade 2 | Delay treatment until resolved to ≤Grade 1. |
| Grade 3 or 4 | Discontinue from treatment. |
| | Periorbital edema |
| Grade 2 | Delay treatment until resolved to ≤Grade 1. Decrease MCS110 1 dose level. |
| Grade 3 | Discontinue from treatment. |
| | Skin (rash) |
| Grade 2 | Delay treatment if persisiting >7 days. Restart when resolved to Grade ≤1. |
| Grade 3 | Delay treatment until resolved to ≤Grade 1. Decrease MCS110 1 dose level. If the AE recurs, discontinue from treatment. |
| Grade 4 | Discontinue from treatment. |
| | Cardiac (myo-/pericarditis) |
| Grade 2 | Delay treatment until ≤Grade 1. Discontinue from treatment if recurrence. |
| Grade 3 lasting > 6 days or Grade 4 | Discontinue from treatment. |

Example 2

After Phase Ib part, if emerging PK, PD, and safety data indicate that a flat dosing strategy of MCS110 is appropriate, then a flat dosing strategy may be implemented in the Phase II part of the study. The PK data obtained during Phase Ib part of this study will be combined with PK data from the other MCS110 clinical studies to assess the flat dosing vs. body-weight based dosing, and a flat dose may be identified for the Phase II part of this stud Example 3

Rnaseq data from the TCGA database shows high level of expression of the surrogate marker for M2 macrophages, CD163, within the patient population defined by the highest level of PD1 expression. An analysis of various tumor types was undertaken to determine expression of CD163 and PD1 in various tumor types. Using RNAseq from the TCGA database and internal database in various cancers including triple negative breast cancer (TNBC), skin, ovarian, pancreatic cancers, glioblastoma (GBM), lung cancer, kidney renal cell carcinoma, diffuse large b cell lymphoma (DLBCL), mesothelioma, and nasopharylngeal carcinoma (NPC), the expression levels of PD-1 in relation to CD163 were observed. Fig a shows the relationship of expression levels of PD-1 in relation to CD163 by sorting expression of PD-1 from high to low. The results show that for high PD-1 expression in general correlates well with high levels of CD163.

Example 4

The M-CSF antibody H-RX1 (an antibody having the heavy chain variable region including the amino acids set forth in SEQ ID NO: 1 and the light chain variable region including the amino acids set forth in SEQ ID NO: 2) in combination with PD-1 BAP049-Clone-E antibody molecule (an antibody molecule having the heavy chain variable region including the amino acids set forth in SEQ ID NO: 11 and the light chain variable region including the amino acids set forth in SEQ ID NO: 12) is administered to patients with advanced triple negative breast cancer (TNBC) who have undergone standard of care therapy. Tumor response is determined locally according to Response Evaluation Criteria in Solid Tumors (RECIST) v1.1 (Therasse et al., (2000) New Guidelines to Evaluate the Response to Treatment in Solid Tumors, Journal of National Cancer Institute, Vol. 92; 205-16); New Guidelines to Evaluate the Response in Solid Tumors, Journal of National Cancer Institute, Vol. 92; 205-16 and revised RECIST guidelines (version 1.1) (Eisenhauer et al 2009) European Journal of Cancer; 45:228-247.

Example 5

The M-CSF antibody H-RX1 (an antibody having the heavy chain variable region including the amino acids set forth in SEQ ID NO: 1 and the light chain variable region including the amino acids set forth in SEQ ID NO: 2) in combination with PD-1 BAP049-Clone-E antibody molecule (an antibody molecule having the heavy chain variable region including the amino acids set forth in SEQ ID NO: 11 and the light chain variable region including the amino acids set forth in SEQ ID NO: 12) is administered to patients with pancreatic cancer. Tumor response will be determined locally according to Response Evaluation Criteria in Solid Tumors (RECIST) v1.1 (Therasse et al., (2000) New Guidelines to Evaluate the Response to Treatment in Solid Tumors, Journal of National Cancer Institute, Vol. 92; 205-16); New Guidelines to Evaluate the Response in Solid Tumors, Journal of National Cancer Institute, Vol. 92; 205-16 and revised RECIST guidelines (version 1.1) (Eisenhauer et al 2009) European Journal of Cancer; 45:228-247.

Example 6

The M-CSF antibody H-RX1 (an antibody having the heavy chain variable region including the amino acids set forth in SEQ ID NO: 1 and the light chain variable region including the amino acids set forth in SEQ ID NO: 2) in combination in combination with PD-1 BAP049-Clone-E antibody molecule (an antibody molecule having the heavy chain variable region including the amino acids set forth in SEQ ID NO: 11 and the light chain variable region including the amino acids set forth in SEQ ID NO: 12) is administered to patients with endometrial carcinoma. Tumor response will be determined locally according to Response Evaluation Criteria in Solid Tumors (RECIST) v1.1 (Therasse et al., (2000) New Guidelines to Evaluate the Response to Treatment in Solid Tumors, Journal of National Cancer Institute, Vol. 92; 205-16); New Guidelines to Evaluate the Response in Solid Tumors, Journal of National Cancer Institute, Vol. 92; 205-16 and revised RECIST guidelines (version 1.1) (Eisenhauer et al 2009) European Journal of Cancer; 45:228-247.

Example 7

The M-CSF antibody H-RX1 (an antibody having the heavy chain variable region including the amino acids set forth in SEQ ID NO: 1 and the light chain variable region including the amino acids set forth in SEQ ID NO: 2) in combination with PD-1 clone E antibody molecule (an antibody molecule having the heavy chain variable region including the amino acids set forth in SEQ ID NO: 11 and the light chain variable region including the amino acids set forth in SEQ ID NO: 12) is administered to patients with melanoma who have undergone standard of care and are resistant to PD-1 or PD-L1 therapy. Tumor response will be determined locally according to Response Evaluation Criteria in Solid Tumors (RECIST) v1.1 (Therasse et al., (2000) New Guidelines to Evaluate the Response to Treatment in Solid Tumors, Journal of National Cancer Institute, Vol. 92; 205-16); New Guidelines to Evaluate the Response in Solid Tumors, Journal of National Cancer Institute, Vol. 92; 205-16 and revised RECIST guidelines (version 1.1) (Eisenhauer et al 2009) European Journal of Cancer; 45:228-247.

Example 8

The M-CSF antibody H-RX1 (an antibody having the heavy chain variable region including the amino acids set forth in SEQ ID NO: 1 and the light chain variable region including the amino acids set forth in SEQ ID NO: 2) in combination with PD-1 BAP049-Clone-E antibody molecule (an antibody molecule having the heavy chain variable region including the amino acids set forth in SEQ ID NO: 11 and the light chain variable region including the amino acids set forth in SEQ ID NO: 12) is administered to patients with advanced triple negative breast cancer (TNBC) who have undergone standard of care therapy and who are refractory or resistant to PD-1 or PD-L1 therapy. Tumor response is determined locally according to Response Evaluation Criteria in Solid Tumors (RECIST) v1.1 (Therasse et al., (2000) New Guidelines to Evaluate the Response to Treatment in Solid Tumors, Journal of National Cancer Institute, Vol. 92; 205-16); New Guidelines to Evaluate the Response in Solid Tumors, Journal of National Cancer Institute, Vol. 92; 205-16 and revised RECIST guidelines (version 1.1) (Eisenhauer et al 2009) European Journal of Cancer; 45:228-247.

Example 9

The M-CSF antibody H-RX1 (an antibody having the heavy chain variable region including the amino acids set forth in SEQ ID NO: 2 and the light chain variable region including the amino acids set forth in SEQ ID NO: 4) in combination with PD-1 BAP049-Clone-E antibody molecule (an antibody molecule having the heavy chain variable region including the amino acids set forth in SEQ ID NO: 37 and the light chain variable region including the amino acids set forth in SEQ ID NO: 47) is administered to patients with either or both of non-small cell lung cancer and squamous cell lung cancer. Tumor response will be determined locally according to Response Evaluation Criteria in Solid Tumors (RECIST) v1.1 (Therasse et al., (2000) New Guidelines to Evaluate the Response to Treatment in Solid Tumors, Journal of National Cancer Institute, Vol. 92; 205-16); New Guidelines to Evaluate the Response in Solid Tumors, Journal of National Cancer Institute, Vol. 92; 205-16 and revised RECIST guidelines (version 1.1) (Eisenhauer et al 2009) European Journal of Cancer; 45:228-247.

All publications, patent applications, patents, and other references mentioned herein are incorporated by reference in their entirety. Other features, objects, and advantages of the invention will be apparent from the description and drawings, and from the claims.

We claim:

1. A method for the treatment of breast cancer, the method comprising administering a therapeutically effective amount of a pharmaceutical combination to a subject in need thereof, wherein the pharmaceutical combination consists of:

i) an isolated antibody molecule capable of binding to a human Programmed Death-1 (PD-1) comprising a heavy chain variable region (VH) comprising a VHCDR1 having the amino acid sequence of SEQ ID NO: 21; a VHCDR2 having the amino acid sequence of SEQ ID NO: 22; and a VHCDR3 having the amino acid sequence of SEQ ID NO: 23; and a light chain variable region (VL) comprising a VLCDR1 having the amino acid sequence of SEQ ID NO: 26, a VLCDR2 having the amino acid sequence of SEQ ID NO: 27, and a VLCDR3 having the amino acid sequence of SEQ ID NO: 28; and ii) an isolated antibody molecule capable of binding to macrophage colony stimulating factor 1 (M-CSF) comprising (a) VH comprising a VHCDR1 having the amino acid sequence of SEQ ID NO: 3, a VHCDR2 having the amino acid sequence of SEQ ID NO: 4 and a VHCDR3 having the amino acid sequence of SEQ ID NO:5; and a VL comprising a VLCDR1 having the amino acid sequence of SEQ ID NO: 6, a VLCDR2 having the amino acid sequence of SEQ ID NO:7 and a VLCDR3 having the amino acid sequence of SEQ ID NO: 8.

2. A method for the treatment of ovarian cancer, the method comprising administering a therapeutically effective amount of a pharmaceutical combination to a subject in need thereof,
wherein the pharmaceutical combination consists of:
i) an isolated antibody molecule capable of binding to a human Programmed Death-1 (PD-1) comprising a heavy chain variable region (VH) comprising a VHCDR1 having the amino acid sequence of SEQ ID NO: 21; a VHCDR2 having the amino acid sequence of SEQ ID NO: 22; and a VHCDR3 having the amino acid sequence of SEQ ID NO: 23; and a light chain variable region (VL) comprising a VLCDR1 having the amino acid sequence of SEQ ID NO: 26, a VLCDR2 having the amino acid sequence of SEQ ID NO: 27, and a VLCDR3 having the amino acid sequence of SEQ ID NO: 28; and
ii) an isolated antibody molecule capable of binding to macrophage colony stimulating factor 1 (M-CSF) comprising (a) VH comprising a VHCDR1 having the amino acid sequence of SEQ ID NO: 3, a VHCDR2 having the amino acid sequence of SEQ ID NO: 4 and a VHCDR3 having the amino acid sequence of SEQ ID NO:5; and a VL comprising a VLCDR1 having the amino acid sequence of SEQ ID NO: 6, a VLCDR2 having the amino acid sequence of SEQ ID NO:7 and a VLCDR3 having the amino acid sequence of SEQ ID NO: 8.

3. A method for the treatment of pancreatic cancer, the method comprising administering a therapeutically effective amount of a pharmaceutical combination to a subject in need thereof,
wherein the pharmaceutical combination consists of:
i) an isolated antibody molecule capable of binding to a human Programmed Death-1 (PD-1) comprising a heavy chain variable region (VH) comprising a VHCDR1 having the amino acid sequence of SEQ ID NO: 21; a VHCDR2 having the amino acid sequence of SEQ ID NO: 22; and a VHCDR3 having the amino acid sequence of SEQ ID NO: 23; and a light chain variable region (VL) comprising a VLCDR1 having the amino acid sequence of SEQ ID NO: 26, a VLCDR2 having the amino acid sequence of SEQ ID NO: 27, and a VLCDR3 having the amino acid sequence of SEQ ID NO: 28; and
ii) an isolated antibody molecule capable of binding to macrophage colony stimulating factor 1 (M-CSF) comprising (a) VH comprising a VHCDR1 having the amino acid sequence of SEQ ID NO: 3, a VHCDR2 having the amino acid sequence of SEQ ID NO: 4 and a VHCDR3 having the amino acid sequence of SEQ ID NO:5; and a VL comprising a VLCDR1 having the amino acid sequence of SEQ ID NO: 6, a VLCDR2 having the amino acid sequence of SEQ ID NO:7 and a VLCDR3 having the amino acid sequence of SEQ ID NO: 8.

4. A method for the treatment of a cancer, the method comprising administering a therapeutically effective amount of a pharmaceutical combination to a subject in need thereof,
wherein the pharmaceutical combination consists of:
i) an isolated antibody molecule capable of binding to a human Programmed Death-1 (PD-1) comprising a heavy chain variable region (VH) comprising a VHCDR1 having the amino acid sequence of SEQ ID NO: 21; a VHCDR2 having the amino acid sequence of SEQ ID NO: 22; and a VHCDR3 having the amino acid sequence of SEQ ID NO: 23; and a light chain variable region (VL) comprising a VLCDR1 having the amino acid sequence of SEQ ID NO: 26, a VLCDR2 having the amino acid sequence of SEQ ID NO: 27, and a VLCDR3 having the amino acid sequence of SEQ ID NO: 28; and
ii) an isolated antibody molecule capable of binding to macrophage colony stimulating factor 1 (M-CSF) comprising (a) VH comprising a VHCDR1 having the amino acid sequence of SEQ ID NO: 3, a VHCDR2 having the amino acid sequence of SEQ ID NO: 4 and a VHCDR3 having the amino acid sequence of SEQ ID NO:5; and a VL comprising a VLCDR1 having the amino acid sequence of SEQ ID NO: 6, a VLCDR2 having the amino acid sequence of SEQ ID NO:7 and a VLCDR3 having the amino acid sequence of SEQ ID NO: 8, and
wherein the cancer is resistant or refractory to PD-1 or human Programmed Death-ligand 1 (PD-L1) therapy.

5. The method of claim 4, wherein the cancer is triple-negative breast cancer (TNBC).

6. The method of claim 4, wherein the cancer is melanoma.

7. The method of claim 4, wherein the PD-1 antibody molecule and the M-CSF antibody are simultaneously or sequentially administrated.

8. A method for the treatment of melanoma cancer, the method comprising administering a therapeutically effective amount of a pharmaceutical combination to a subject in need thereof,
wherein the pharmaceutical combination consists of:
i) an isolated antibody molecule capable of binding to a human Programmed Death-1 (PD-1) comprising a heavy chain variable region (VH) comprising a VHCDR1 having the amino acid sequence of SEQ ID NO: 21; a VHCDR2 having the amino acid sequence of SEQ ID NO: 22; and a VHCDR3 having the amino acid sequence of SEQ ID NO: 23; and a light chain variable region (VL) comprising a VLCDR1 having the amino acid sequence of SEQ ID NO: 26, a VLCDR2 having the amino acid sequence of SEQ ID NO: 27, and a VLCDR3 having the amino acid sequence of SEQ ID NO: 28; and
ii) an isolated antibody molecule capable of binding to macrophage colony stimulating factor 1 (M-CSF) comprising (a) VH comprising a VHCDR1 having the amino acid sequence of SEQ ID NO: 3, a VHCDR2 having the amino acid sequence of SEQ ID NO: 4 and a VHCDR3 having the amino acid sequence of SEQ ID NO:5; and a VL comprising a VLCDR1 having the amino acid sequence of SEQ ID NO: 6, a VLCDR2 having the amino acid sequence of SEQ ID NO:7 and a VLCDR3 having the amino acid sequence of SEQ ID NO: 8.

9. A method for treatment of endometrial cancer, the method comprising a therapeutically effective amount of a pharmaceutical combination to a subject in need thereof,
wherein the pharmaceutical combination consists of:
i) an isolated antibody molecule capable of binding to a human Programmed Death-1 (PD-1) comprising a heavy chain variable region (VH) comprising a VHCDR1 having the amino acid sequence of SEQ ID NO: 21; a VHCDR2 having the amino acid sequence of SEQ ID NO: 22; and a VHCDR3 having the amino acid sequence of SEQ ID NO: 23; and a light chain variable region (VL) comprising a VLCDR1 having the amino acid sequence of SEQ ID NO: 26, a VLCDR2 having the amino acid sequence of SEQ ID NO: 27, and a VLCDR3 having the amino acid sequence of SEQ ID NO: 28; and
ii) an isolated antibody molecule capable of binding to macrophage colony stimulating factor 1 (M-CSF) comprising (a) VH comprising a VHCDR1 having the amino acid sequence of SEQ ID NO: 3, a VHCDR2 having the amino acid sequence of SEQ ID NO: 4 and a VHCDR3 having the amino acid sequence of SEQ ID NO:5, and a VL comprising a VLCDR1 having the amino acid sequence of SEQ ID NO: 6, a VLCDR2 having the amino acid sequence of SEQ ID NO:7 and a VLCDR3 having the amino acid sequence of SEQ ID NO: 8.

* * * * *